US 12,307,809 B2

(12) United States Patent
Matsuda et al.

(10) Patent No.: US 12,307,809 B2
(45) Date of Patent: *May 20, 2025

(54) PHOTOGRAPHING APPARATUS AND AUTHENTICATION APPARATUS

(71) Applicant: Hitachi, Ltd., Tokyo (JP)

(72) Inventors: Yusuke Matsuda, Tokyo (JP); Naoto Miura, Tokyo (JP); Akio Nagasaka, Tokyo (JP); Yo Nonomura, Tokyo (JP); Keiichiro Nakazaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/429,809

(22) Filed: Feb. 1, 2024

(65) Prior Publication Data

US 2024/0221420 A1    Jul. 4, 2024

Related U.S. Application Data

(63) Continuation of application No. 17/642,630, filed as application No. PCT/JP2020/032464 on Aug. 27, 2020, now Pat. No. 11,928,889.

(30) Foreign Application Priority Data

Dec. 4, 2019    (JP) .................................. 2019-219636

(51) Int. Cl.
*G06V 40/145*    (2022.01)
*G06V 10/141*    (2022.01)
(Continued)

(52) U.S. Cl.
CPC .......... *G06V 40/145* (2022.01); *G06V 10/141* (2022.01); *G06V 10/143* (2022.01); *H04N 23/56* (2023.01); *H04N 23/74* (2023.01)

(58) Field of Classification Search
CPC .......... A61L 2/20; A61L 2/22; A61L 2202/25; A61L 2209/22; A61L 9/00; A61L 9/015;
(Continued)

(56) References Cited

U.S. PATENT DOCUMENTS 11,928,889 B2*   3/2024   Matsuda ................ H04N 23/74
2009/0174766 A1   7/2009   Kiyomizu et al.
(Continued)

FOREIGN PATENT DOCUMENTS

EP    1 894 524 A1    3/2008
JP    2008-212311 A    9/2008
(Continued)

OTHER PUBLICATIONS

International Search Report (PCT/ISA/210) issued in PCT Application No. PCT/JP2020/032464 dated Oct. 6, 2020 with English translation (five (5) pages).
(Continued)

*Primary Examiner* — Kathleen M Walsh
(74) *Attorney, Agent, or Firm* — Crowell & Moring LLP

(57) ABSTRACT

A photographing apparatus includes: an imaging unit which is arranged at a position opposed to a plurality of fingers to be presented, and is configured to image the plurality of fingers; and a plurality of light sources which are arranged in plurality in an array direction of the plurality of fingers, and are configured to irradiate the plurality of fingers with light from an outside of an opposing region in which the imaging unit is opposed to the plurality of fingers toward an inside of the opposing region.

28 Claims, 13 Drawing Sheets

(51) Int. Cl.
*G06V 10/143* (2022.01)
*H04N 23/56* (2023.01)
*H04N 23/74* (2023.01)

(58) Field of Classification Search
CPC ... A61L 9/03; A61L 9/04; A61L 9/122; A61L 9/145; B01F 25/72; C01B 11/022; F24F 6/00; A61B 5/0059; A61B 5/1171; G06F 21/32; G06V 10/141; G06V 10/143; G06V 40/1318; G06V 40/145; G06V 40/70; H04N 23/56; H04N 23/74
USPC .......................................................... 348/77
See application file for complete search history.

(56) References Cited

U.S. PATENT DOCUMENTS

| | | | | |
|---|---|---|---|---|
| 2013/0027184 A1* | 1/2013 | Endoh | ................. | G06V 40/145 340/5.83 |
| 2015/0252980 A1 | 9/2015 | Maeda et al. | | |
| 2018/0239944 A1* | 8/2018 | Ohno | ................. | A61B 5/0075 |
| 2018/0247142 A1 | 8/2018 | Oda et al. | | |
| 2019/0125221 A1* | 5/2019 | Kobayashi | ............ | G06T 1/0007 |
| 2019/0340344 A1 | 11/2019 | Choi et al. | | |
| 2020/0311370 A1* | 10/2020 | Hu | ........................ | G06V 40/10 |

FOREIGN PATENT DOCUMENTS

| | | |
|---|---|---|
| JP | 2009-9354 A | 1/2009 |
| JP | 2009-271748 A | 11/2009 |
| JP | 2015-170320 A | 9/2015 |
| JP | 2017-91186 A | 5/2017 |
| KR | 101720957 B1 | 3/2017 |
| WO | WO 2009/014194 A1 | 1/2009 |
| WO | WO 2017/047091 A1 | 3/2017 |
| WO | WO 2017/082100 A1 | 5/2017 |

OTHER PUBLICATIONS

Japanese-language Written Opinion (PCT/ISA/237) issued in PCT Application No. PCT/JP2020/032464 dated Oct. 6, 2020 (four (4) pages).
Extended European Search Report issued in European Application No. 20896642.4 dated Dec. 6, 2023 (9 pages).

* cited by examiner

PHOTOGRAPHING APPARATUS AND AUTHENTICATION APPARATUS

CROSS REFERENCE TO RELATED APPLICATIONS

This application is a Continuation of U.S. patent application Ser. No. 17/642,630, filed Mar. 11, 2022, which is a 371 of International Application No. PCT/JP2020/032464, filed Aug. 27, 2020, which claims priority to Japanese Patent Application No. 2019-219636, filed Dec. 4, 2019, the disclosures of all of which are expressly incorporated by reference herein.

BACKGROUND

This invention relates to a photographing apparatus which photographs a living body, and an authentication apparatus which photographs and authenticates a living body.

There has been proposed a biometric authentication technology with use of a biometric image (blood vessel image) obtained by photography utilizing a difference in characteristic of absorbing near-infrared light of hemoglobin in blood and the other body tissues. A living body is irradiated with the near-infrared light having a wavelength with a high absorption factor by hemoglobin, and transmitted or reflected light is imaged to obtain a blood vessel image. There is an individually different blood vessel pattern under a skin surface of a finger, and highly accurate authentication can be achieved by clearly imaging the blood vessel pattern.

One of methods of photographing a blood vessel image for achieving the authentication technology with use of the blood vessel image of a finger with a compact apparatus size is a reflection method. The reflection method is a method in which a light source and an imaging unit are arranged in proximity to each other, the ball of the finger is irradiated with irradiation light from the light source, and reflected light is imaged to obtain the blood vessel image. The biometric authentication apparatus of JP 2015-170320 A below, which adopts the reflection method, includes a light source which is provided on a surface of a substrate and emits light, and a diffraction optical element which has a plurality of diffraction gratings with different pitch and rotating direction, and diffracts the light into illumination light with which an illumination region of an illuminating target is irradiated, and the illumination region is configured so as to be larger than an area occupied by the diffraction optical element and the light source provided on a plane parallel to the surface of the substrate.

Further, in order to achieve higher authentication accuracy, an authentication method using a blood vessel image obtained by photographing not only one finger but also a plurality of fingers at the same time is effective. The reflection method can photograph the blood vessel image of the plurality of fingers at the same time even under a state in which the living body is not in contact with the apparatus, and hence both of high convenience and downsizing of the apparatus can be achieved.

A surface shape of a finger is stereoscopic and has many curved surfaces. Thus, in a reflection method, a difference in amount of reflected light occurs for each part of the finger, and a sufficient brightness cannot be obtained in regions of finger, such as the fingertip and side surfaces (near the contour) of the finger. Accordingly, there is a problem in that it is difficult to take a clear blood vessel image. In an unclear blood vessel image with an insufficient brightness, the finger region cannot be detected accurately, and there is a fear in that the authentication accuracy may be reduced. Consequently, particularly in a case in which a blood vessel image is to be taken of a plurality of fingers at the same time, it is a problem to clearly photograph blood vessels of all the fingers to be photographed.

SUMMARY

It is an object of this invention to inhibit an insufficient amount of light on a subject to be photographed.

A photographing apparatus which is an aspect of the disclosure in the present application comprises: an imaging unit which is arranged at a position opposed to a plurality of fingers to be presented, and is configured to image the plurality of fingers; and a plurality of light sources which are arranged in plurality in an array direction of the plurality of fingers, and are configured to irradiate the plurality of fingers with light from an outside of an opposing region in which the imaging unit is opposed to the plurality of fingers toward an inside of the opposing region.

An authentication apparatus which is an aspect of the disclosure in the present application comprises: an imaging unit which is arranged at a position opposed to a plurality of fingers to be presented, and is configured to image the plurality of fingers; a plurality of light sources which are arranged in plurality in an array direction of the plurality of fingers, and are configured to irradiate the plurality of fingers with light from an outside of an opposing region in which the imaging unit is opposed to the plurality of fingers toward an inside of the opposing region; an image processing module configured to generate image data of the plurality of fingers based on an output signal from the imaging unit; and an authentication module configured to authenticate the plurality of fingers based on first image data of the plurality of fingers generated by the image processing module, and second image data of the plurality of fingers generated by the image processing module.

According to the representative embodiment of this invention, an insufficient amount of light on the subject to be photographed can be inhibited. Other objects, configurations, and effects than those described above are clarified by the following description of an embodiment.

DETAILED DESCRIPTION OF THE EMBODIMENTS

First Embodiment

<Configuration Examples of Photographing Apparatus and Authentication Apparatus>

Figure 1:
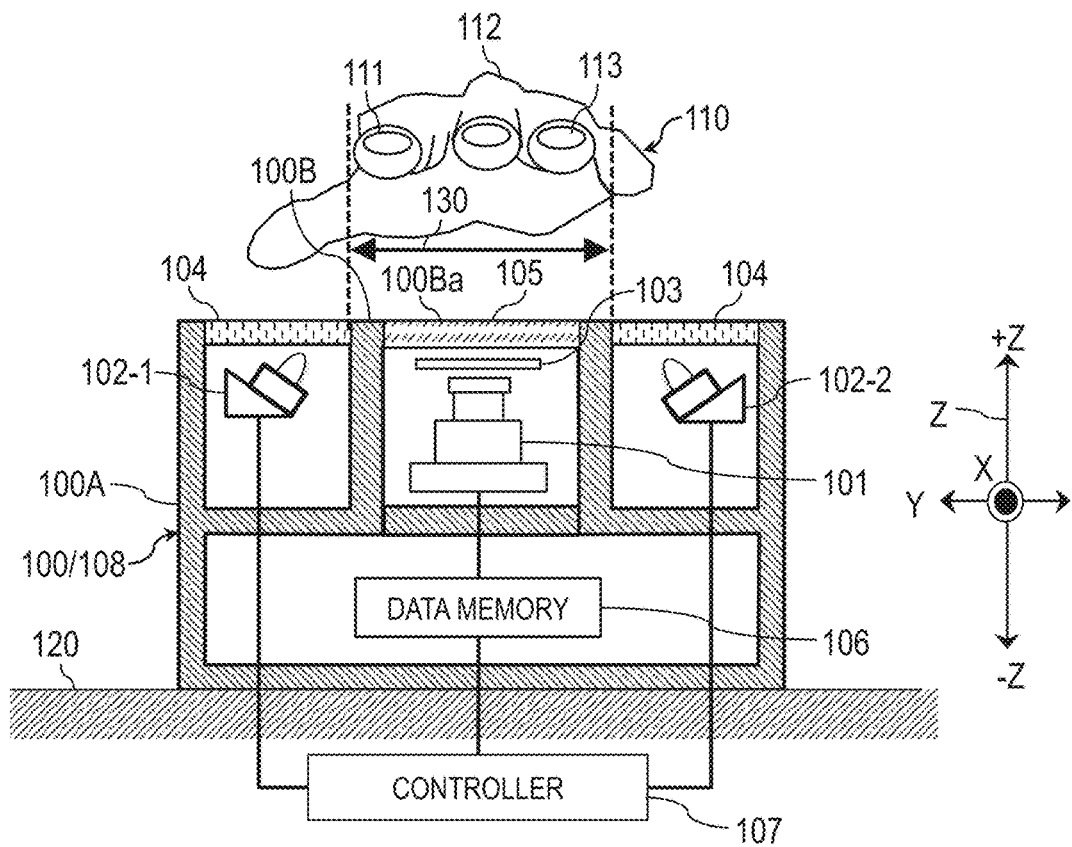
FIG. 1 is an explanatory diagram for illustrating Configuration Example 1 of a photographing apparatus and an authentication apparatus according to a first embodiment of this invention.

FIG. 1 is an explanatory diagram for illustrating Configuration Example 1 of a photographing apparatus and an authentication apparatus according to a first embodiment of this invention. A photographing apparatus 100 photographs fingers of a hand 110 placed as a subject over an upper plate portion 100B of a housing 100A. In the first embodiment, as an example, an index finger 111, a middle finger 112, and a third finger 113 are the subject (object to be imaged). It is only required that the fingers 111 to 113 as the subject include two or more of ten fingers of both hands 110. Surfaces of the fingers 111 to 113 on the back side of the hand 110 are referred to as front surfaces of the fingers 111 to 113, and surfaces of the fingers 111 to 113 on the palm side of the hand 110 are referred to as back surfaces of the fingers 111 to 113.

In FIG. 1, the photographing apparatus 100 includes the housing 100A, an imaging unit 101, light sources 102, and a data memory 106. An apparatus obtained by coupling a controller 107 to the photographing apparatus 100 is an authentication apparatus 108.

The housing 100A is installed or placed (hereinafter collectively referred to as "mounted") on, for example, a mounting surface 120. The mounting surface 120 may be the ground, a ceiling surface, or a surface of a table parallel to the ground, for example, a desk, or may be a surface perpendicular to the ground, for example, a wall. An axis orthogonal to the mounting surface 120 is defined as a Z axis, a direction of being separated from the mounting surface 120 in the Z axis is defined as a +Z direction, and a direction of approaching the mounting surface 120 is defined as a −Z direction. Further, the mounting surface 120 is parallel to an XY plane. The XY plane is a plane formed by an X axis and a Y axis. As illustrated in FIG. 1, the photographing apparatus 100 and the authentication apparatus 108 are mounted so that the hand 110 is placed over the upper plate portion 100B. In this case, the X axis is a longitudinal direction of the fingers at the time when the hand 110 is placed. The Y axis is an array direction of the fingers 111 to 113.

The housing 100A includes the imaging unit 101 and a plurality of light sources 102 (in FIG. 1, light sources 102-1 and 102-2) therein. The light sources 102-1 and 102-2 are simply referred to as the light sources 102 when no distinction is made therebetween. Further, between the imaging unit 101 and the upper plate portion 100B of the housing 100A, a first optical filter 103 is provided. The imaging unit 101 receives subject light that has passed through the first optical filter 103. The subject light is light (reflected light) obtained by irradiation light from the light sources 102 being reflected by the subject.

The imaging unit 101 and the upper plate portion 100B of the housing 100A are opposed to the presented hand 110. In particular, of the upper plate portion 100B, a surface opposed to the fingers 111 to 113 is referred to as an opposing surface 100Ba. A region in the +Z direction from the opposing surface 100Ba is an opposing region 130 in which the presented fingers 111 to 113 are opposed to the imaging unit 101 and the opposing surface 100Ba. A width in an X-axis direction of the opposing surface 100Ba and the opposing region 130 is, for example, a width encompassing a length from the fingertips to the finger bases of the fingers 111 to 113.

Further, in a region of the upper plate portion 100B that exists in the +Z direction from the imaging unit 101, there is provided a light transmitting plate 105 which transmits light obtained by the irradiation light from the light sources 102 being reflected by a living body, for example, the fingers 111 to 113. The light transmitting plate 105 is formed of a transparent member made of, for example, acryl or glass. Still further, a film which passes only light having a particular wavelength may be bonded to the light transmitting plate 105. With this configuration, a state in which it is difficult to visually check the inside of the photographing apparatus 100 from the outside can be achieved.

Still further, in regions of the upper plate portion 100B that exist in the +Z direction from the light sources 102, second optical filters 104 are provided. The subject is irradiated with light from the light sources 102 that has passed through the second optical filters 104. The second optical filters 104 may be a light diffusion filter. With this configuration, the light sources 102 can irradiate the subject over a wide range with the irradiation light having a uniform intensity.

Alternatively, the second optical filters 104 may be a polarizing filter. With this configuration, of components of the light irradiated on and reflected by the living body, for example, the fingers 111 to 113, components specularly reflected on a skin surface can be reduced. Consequently, the photographing apparatus 100 can take a blood vessel image of the living body more clearly. Still alternatively, the second optical filters 104 may be a band pass filter which transmits only a particular wavelength of the irradiation light from the light sources 102. With this configuration, the imaging unit 101 can be inhibited from receiving unnecessary ambient light.

The imaging unit 101 is formed of an imaging element, for example, a complementary metal oxide semiconductor (CMOS) image sensor or a charge coupled device (CCD) image sensor. An imaging surface of the imaging unit 101 is opposed to the upper plate portion 100B.

The imaging unit 101 receives, on the imaging surface, light that enters from the outside of the housing 100A through the light transmitting plate 105 of the upper plate portion 100B and the first optical filter 103, and photoelectrically converts the light. The imaging unit 101 is coupled to the data memory 106, and stores image data obtained as a result of the photoelectric conversion in the data memory 106. The image data may be image data (finger blood vessel image data) showing blood vessels of the fingers, or image data (fingerprint image data) showing fingerprints. The finger blood vessel image data and the fingerprint image data are collectively referred to as finger image data. The data memory 106 is coupled to the controller 107. In this specification, the fingerprints are patterns of at least the fingertips (balls of fingers), and may include patterns of the back surfaces of the fingers from the fingertips to the bases of the fingers.

The light sources 102 irradiates the subject that exists in the +Z direction from the upper plate portion 100B with light via the second optical filters 104. In the case in which the blood vessels of the fingers are to be photographed, the irradiation light from the light sources 102 is, for example, near-infrared light. Further, in the case in which the fingerprints are to be photographed, the irradiation light from the light sources 102 is, for example, visible light (for example, blue or green). The light sources 102 are provided at positions that sandwich the imaging unit 101. In other words, the light sources 102 are arrayed in a Y-axis direction. The light sources 102 are arranged at positions between the fingertips to the finger bases in the X-axis direction. In this manner, the light sources 102 irradiate the fingers 111 to 113 with light from the outside of the opposing region 130 toward the inside of the opposing region 130.

Breadths of the irradiation light from the light sources 102 are referred to as shafts of light. The shafts of light are ranges in which the fingers 111 to 113 serving as the subject are irradiated. Stated differently, the light sources 102 are arranged so that the shafts of light thereof encompass the fingers 111 to 113. A center axis of a shaft of light is referred to as an optical axis. The optical axis is an irradiation direction of light. The optical axis is not parallel to the Z axis, but is a direction inclined by a predetermined angle from the Z axis (+Z direction) toward the imaging unit 101 side.

In the case in which the optical axis is parallel to the Z axis, the side surface on a thumb side of the index finger 111 and the side surface on a little finger side of the third finger 113 are irradiated with a sufficient amount of light, but the middle finger 112, the side surface on the middle finger side of the index finger 111, and the side surface on the middle finger side of the third finger 113 are irradiated with an insufficient amount of light. Accordingly, the irradiation direction is inclined toward the imaging unit 101 side by the predetermined angle to irradiate each of the index finger 111, the middle finger 112, and the third finger 113 with a sufficient amount of light, and hence inhibit an insufficient amount of light on the side surface of any one of the index finger 111, the middle finger 112, and the third finger 113.

The light sources 102 are coupled to the controller 107 provided on the outside of the housing 100A. The controller 107 controls amounts of light irradiated from the light sources 102. The controller 107 also detects positions of the fingers 111 to 113, and extracts features of the blood vessels or the fingerprints in the fingers 111 to 113 from the finger image data. The controller 107 may further authenticate a plurality of types of finger image data stored in the data memory 106. Specifically, for example, the controller 107 acquires two sets of finger image data from the data memory 106, and authenticates whether the index finger 111, the middle finger 112, and the third finger 113 in the both sets of finger image data are the index finger 111, the middle finger 112, and the third finger 113 of the same person based on the features of the blood vessels of the fingers and the features of the fingerprints.

Figure 2:
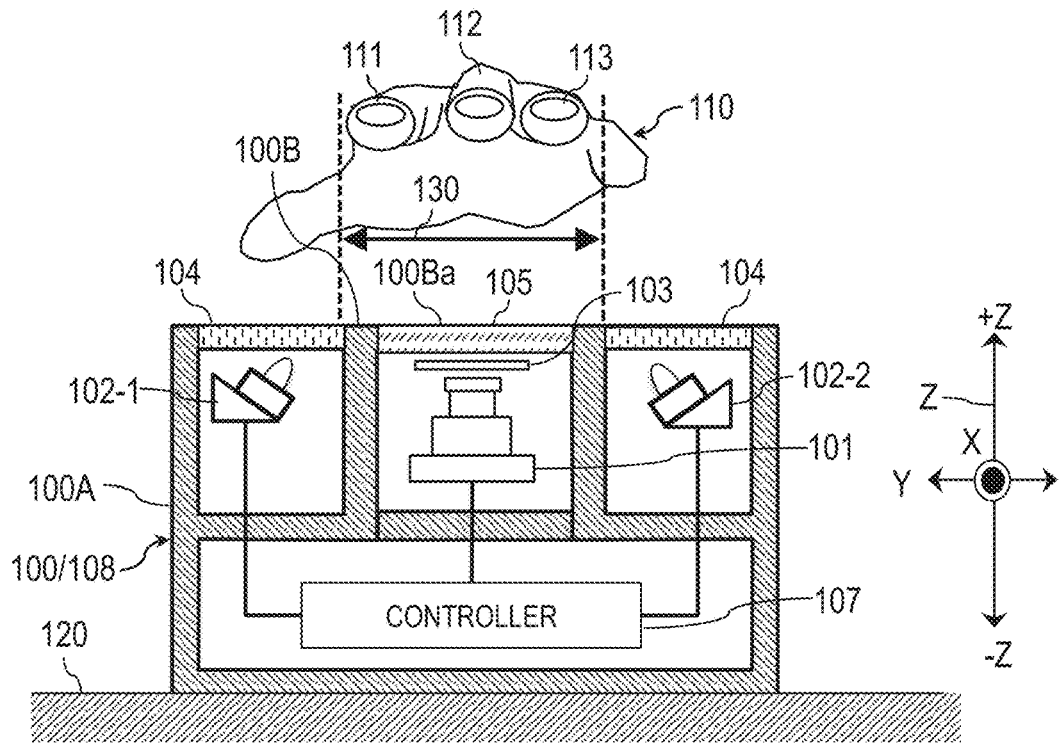
FIG. 2 is an explanatory diagram for illustrating Configuration Example 2 of the photographing apparatus and the authentication apparatus according to the first embodiment.

FIG. 2 is an explanatory diagram for illustrating Configuration Example 2 of the photographing apparatus 100 and the authentication apparatus 108 according to the first embodiment. The photographing apparatus 100 and the authentication apparatus 108 illustrated in FIG. 2 are an example in which the controller 107 illustrated in FIG. 1 is installed inside the housing 100A. The apparatus is the photographing apparatus 100 when the controller 107 has no authentication function, and the apparatus is the authentication apparatus 108 when the controller 107 has an authentication function.

Figure 3:
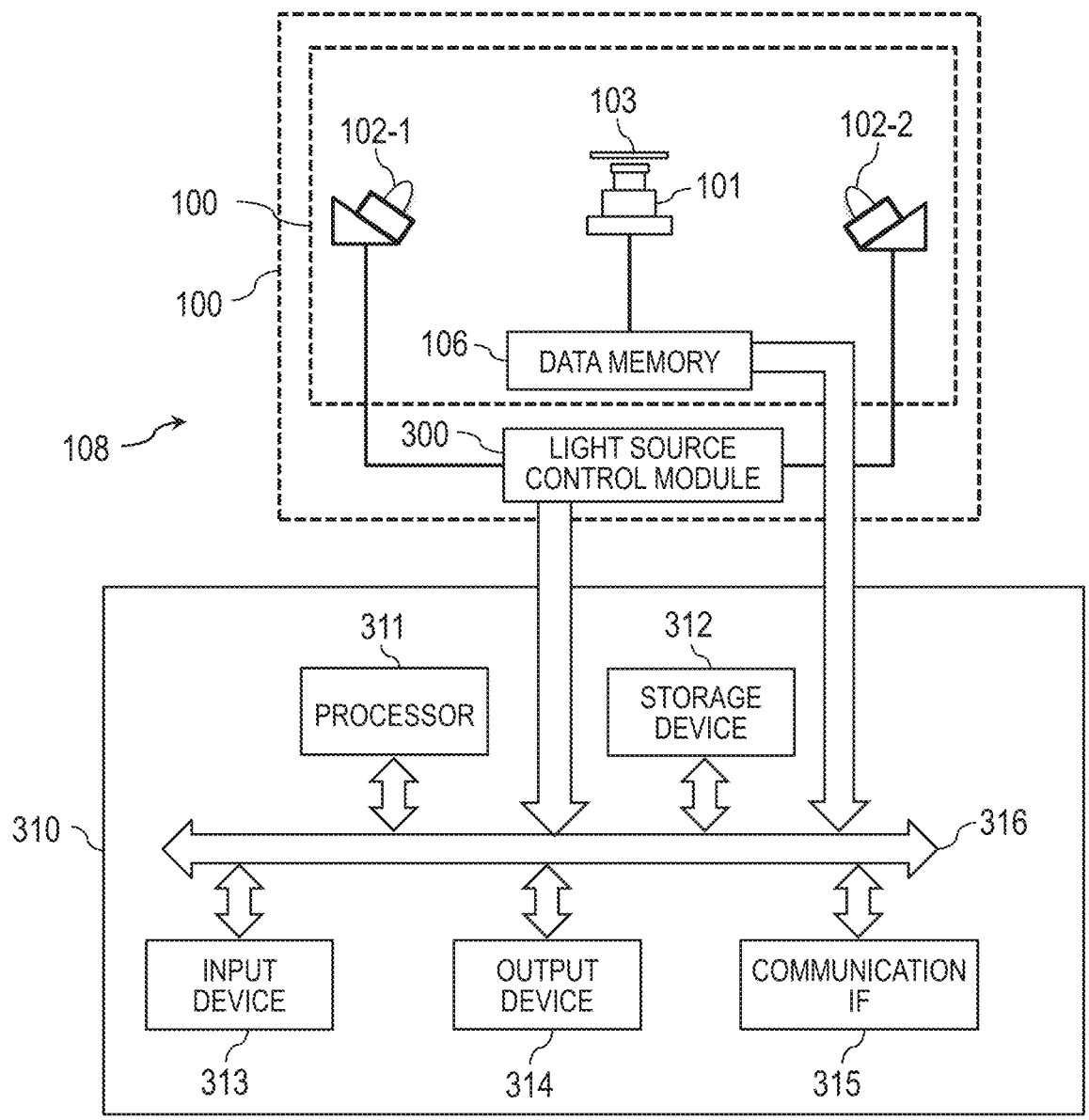
FIG. 3 is a block diagram for illustrating Block Configuration Example 1 of the photographing apparatus and the authentication apparatus according to the first embodiment.

FIG. 3 is a block diagram for illustrating Block Configuration Example 1 of the photographing apparatus 100 and the authentication apparatus 108 according to the first embodiment. The photographing apparatus 100 includes a light source control module 300. The light source control module 300 controls an amount of irradiation light from the light sources 102. The light source control module 300 is included in the controller 107 illustrated in FIG. 1 and FIG. 2. A computer 310 includes an authentication function. The computer 310 is included in the controller 107 illustrated in FIG. 1 and FIG. 2.

The computer 310 includes a processor 311, a storage device 312, an input device 313, an output device 314, and a communication interface (communication IF) 315. The processor 311, the storage device 312, the input device 313, the output device 314, and the communication IF 315 are coupled to one another through a bus 316. The processor 311 is configured to control the computer 310. The storage device 312 serves as a work area for the processor 311. The storage device 312 is also a non-transitory or transitory recording medium configured to store various programs and various kinds of data. Examples of the storage device 312 include a read only memory (ROM), a random access memory (RAM), a hard disk drive (HDD), and a flash memory. The input device 313 is configured to input data. Examples of the input device 313 include a keyboard, a mouse, a touch panel, a numeric keypad, and a scanner The output device 314 is configured to output data. Examples of the output device 314 include a display, a printer, and a speaker. The communication IF 315 is coupled to the network 110, and is configured to transmit and receive data.

Examples of the programs stored in the storage device 312 described above include an image processing program, a light source control program, and an authentication program. The image processing program is a program for causing the processor 311 to generate image data based on an output signal from the imaging unit 101. The light source control program is a program for causing the processor 311 to increase or reduce amounts of irradiation light from the light sources 102. The authentication program is a program for causing the processor 311 to authenticate the identity of two sets of finger image data stored in the storage device 312. The description has been given of an example of implementing the functions of image processing, light source control, and authentication by software, but the functions of image processing, light source control, and authentication may be implemented by dedicated circuits.

In other words, the photographing apparatus 100 not including the light source control module 300 is the photographing apparatus 100 illustrated in FIG. 1, and the photographing apparatus 100 including the light source control module 300 is the photographing apparatus 100 illustrated in FIG. 2. Further, the authentication apparatus 108 having the functions of image processing, light source control, and authentication includes the light source control module 300 and the computer 310, and corresponds to the authentication apparatus 108 of FIG. 1 and FIG. 2.

Figure 4:
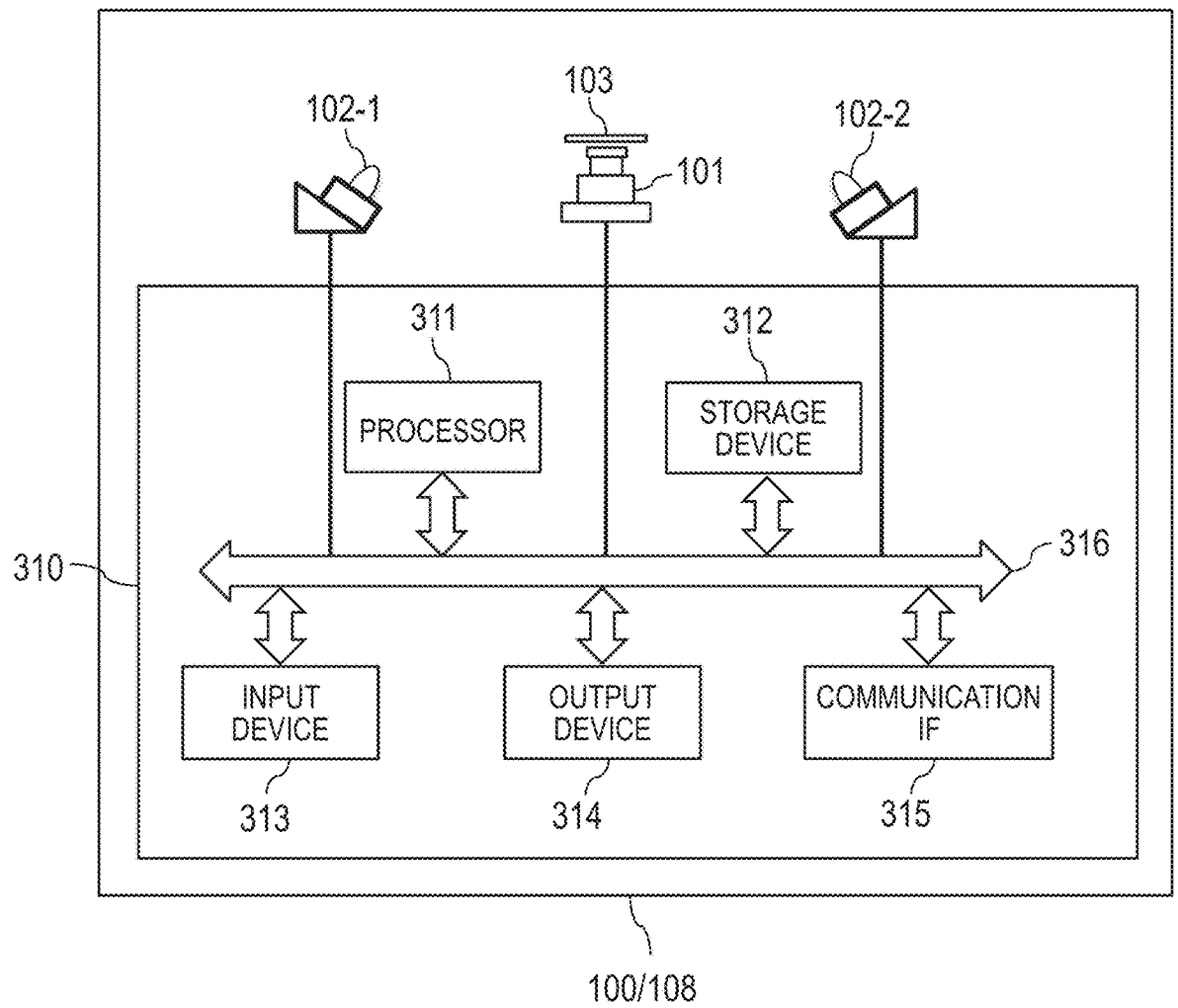
FIG. 4 is a block diagram for illustrating Block Configuration Example 2 of the photographing apparatus and the authentication apparatus according to the first embodiment.

FIG. 4 is a block diagram for illustrating Block Configuration Example 2 of the photographing apparatus 100 and the authentication apparatus 108 according to the first embodiment. The photographing apparatus 100 and the authentication apparatus 108 illustrated in FIG. 4 includes a computer 310. The data memory 106 is implemented by the storage device 312. The light source control module 300 is implemented by causing the processor 311 to execute the program stored in the storage device 312. Further, the authentication function is implemented by causing the processor 311 to execute the program stored in the storage device 312. The apparatus is the photographing apparatus 100 when the computer 310 has no authentication function, and the apparatus is the authentication apparatus 108 when the computer 310 has an authentication function.

At least one of the light sources 102 illustrated in FIG. 1 to FIG. 4 may be a visible light source. In this case, the controller 107 may control the visible light source to emit light of different colors when the hand 110 is detected during standby, during authentication processing, when the authentication is successful, and when the authentication is unsuccessful, respectively. With this configuration, a user can visually check an authentication state.

Further, in a stage prior to the authentication, the computer 310 may register a user ID and a personal identification number in association with the finger image data of the user in the storage device 312 by receiving the user ID and the personal identification number via the input device 313, or wirelessly receiving the user ID and the personal identification number from an IC chip or a communication terminal possessed by the user via the communication IF 315.

Still further, the computer 310 may identify the finger image data associated with the user ID and the personal identification number, which is stored in the storage device 312, by acquiring the user ID and the personal identification number via the input device 313 or the communication IF 315 as described above, and the finger image data, to thereby authenticate both sets of finger image data (what is called 1:1 authentication). The computer 310 may identify the finger image data that matches currently input finger image data from sets of finger image data stored in the storage device 312 (what is called 1:N authentication).

Yet further, in the photographing apparatus 100 and the authentication apparatus 108 illustrated in FIG. 1 to FIG. 4, the irradiation light from the light sources 102 may include light having a plurality of different wavelengths. For example, in a case in which the imaging unit 101 is formed of, for example, a plurality of sensors having different wavelength sensitivity characteristics as in a color camera, the imaging unit 101 irradiates the light having the plurality of different wavelengths from the light sources 102 at the same time to photograph the fingers 111 to 113 with the reflected light from the fingers 111 to 113. With this configuration, the controller 107 can efficiently separate finger regions irradiated with the light from the light sources 102 and a background region not irradiated with the light by utilizing the difference of the wavelength sensitivity characteristics of the respective sensors.

Yet further, the light sources 102 may irradiate not only the near-infrared light for photographing the blood vessels but also light having a wavelength suitable for photographing the fingerprints which are the uneven structure on the surface of the skin. In this case, the computer 310 can perform multimodal authentication utilizing the blood vessels and the fingerprints of the fingers 111 to 113. In the case in which the light having a different wavelength is used for each of the light sources 102 as described above, the second optical filters 104 may be band pass filters that transmit only the respective wavelengths. Alternatively, each of the second optical filters 104 may be a band pass filter that transmits one wide range of wavelength bands encompassing the plurality of wavelengths.

<Examples of Irradiation from Light Sources 102>

In the case in which a single light source is arranged immediately below the plurality of fingers 111 to 113, that is, in the vicinity of the imaging unit 101, the vicinity of the center of the ball of each of the fingers 111 to 113 is regarded as a substantially horizontal surface and is irradiated with strong irradiation light. As a result, the imaging unit 101 can receive reflected light having a sufficient brightness. In contrast, the vicinity of the contour and the vicinity of the fingertip of each of the other fingers that are far from the balls of the fingers 111 to 113 are hardly irradiated with the irradiation light due to curved shapes of the fingers 111 to 113. With such arrangement of the single light source, the imaging unit 101 cannot receive reflected light having a sufficient brightness to be darkened, and the controller 107 cannot generate finger image data that forms a clear finger image.

Figure 5:
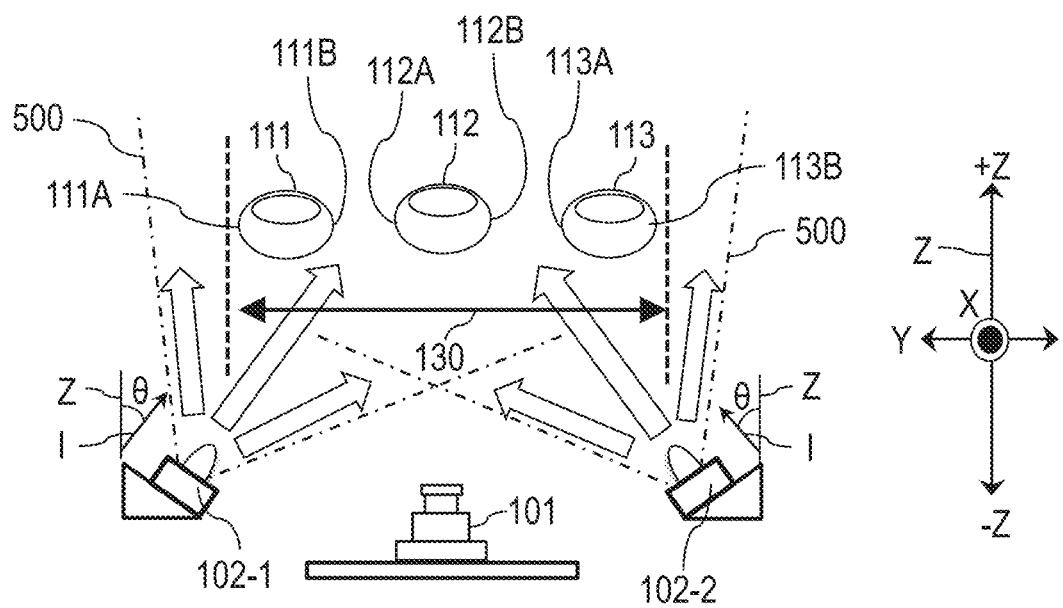
FIG. 5 is an explanatory diagram for illustrating Example 1 of irradiation from the light sources.

FIG. 5 is an explanatory diagram for illustrating Example 1 of irradiation from the light sources 102. The light sources 102 are arranged in advance to be located further on the outside of fingers on the outside along an array direction Y of the fingers 111 to 113. An optical axis I is a direction inclined by a predetermined angle θ about the X axis from the Z axis toward a direction in which the other light source 102 exists. With this configuration, the light source 102-1 irradiates the back surface and a side surface 111A on the thumb side of the index finger 111, the back surface and a side surface 112A on the index finger side of the middle finger 112, and the back surface and a side surface 113A on the middle finger side of the third finger 113 (included in a shaft 500 of light). Similarly, the light source 102-2 irradiates the back surface and a side surface 113B on the little finger side of the third finger 113, the back surface and a side surface 112B on the third finger side of the middle finger 112, and the back surface and a side surface 111B on the middle finger side of the index finger 111.

As described above, each of the light sources 102 can irradiate the vicinity of the contour of a finger that is far from the position of the light source 102 with sufficient light. Instead of inclining the optical axis I toward the imaging unit 101 side, a lens with which the amount of irradiation light becomes larger as the distance from an irradiation position becomes longer may be used. With this configuration, the light source 102 can irradiate the vicinity of the contour of the finger that is far from the irradiation position with a sufficient amount of light.

As described above, the irradiation light from the light sources 102 strongly impinges not only on the vicinity of the center of the ball of each of the fingers 111 to 113 but also on the vicinity of the contour of each of the finger 111 to 113, and the imaging unit 101 receives the reflected light having the sufficient brightness over the whole of the finger regions. Consequently, the controller 107 can generate finger image data that forms a clear finger image. When a plurality of light sources 102 irradiate at the same time, there is a region in which irradiation light beams from the respective light sources overlap. Thus, considering the fact that the irradiation light beams overlap and intensify each other, the arrangement of the light sources 102 is determined and the controller 107 adjusts intensities of the irradiation light beams so that all regions of all the fingers have a uniform brightness. Specifically, for example, the light sources 102 are arranged so that distances to the closest finger are the same or a difference between the distances is within a tolerance range, and so that distances to the farthest finger are the same or a difference between the distances is within the tolerance range.

Figure 6:
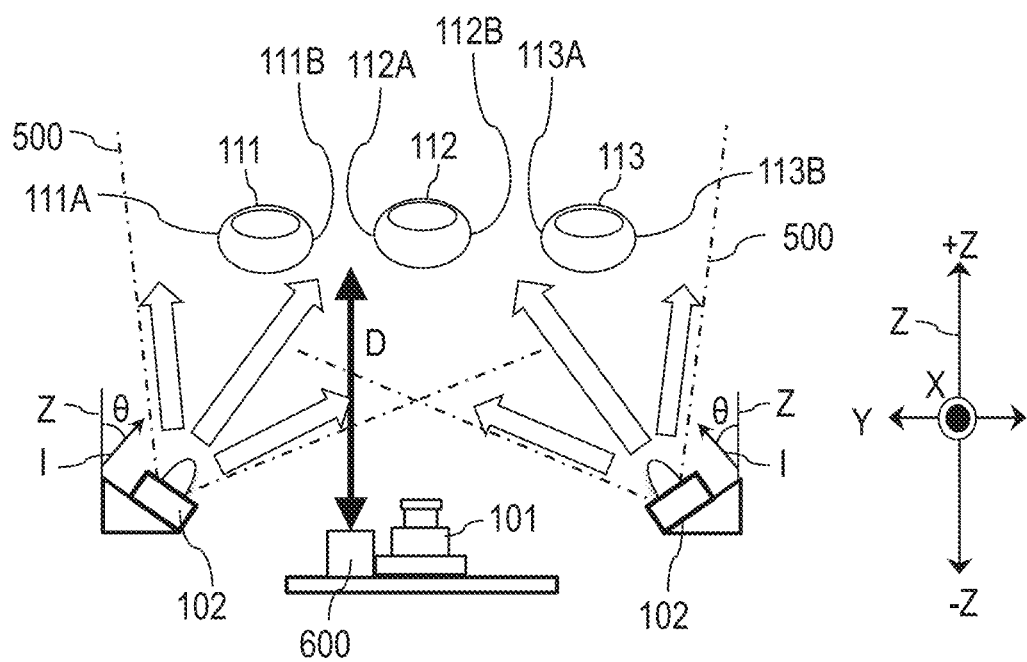
FIG. 6 is an explanatory diagram for illustrating Example 2 of irradiation from the light sources.

FIG. 6 is an explanatory diagram for illustrating Example 2 of irradiation from the light sources 102. FIG. 6 is an example in which a distance sensor 600 is provided in the vicinity of the imaging unit 101 in the configuration of FIG. 5. The distance sensor 600 is mounted at a position in the housing 100A at which a distance in the +Z direction from the mounting surface 120 is the same. The distance sensor 600 detects a distance D to the fingers 111 to 113, that is, the distance D between the fingers 111 to 113 and the imaging unit 101. Specifically, for example, the distance sensor 600 detects the distance D to the fingers 111 to 113 based on a difference in time from when the fingers 111 to 113 are irradiated with infrared light to when reflected light is received from the fingers 111 to 113. Alternatively, the distance sensor 600 may detect the distance D to the fingers 111 to 113 based on a capacitance between the fingers 111 to 113 and the imaging unit 101.

In this manner, the controller 107 increases or reduces the amounts of light from the light sources 102 depending on the distance D. For example, the controller 107 reduces the amounts of irradiation light of the light sources 102 as the distance D becomes shorter, and increases the amounts of irradiation light of the light sources 102 as the distance D becomes longer.

<Procedure of Registration Processing of Finger Image Data>

Figure 7:
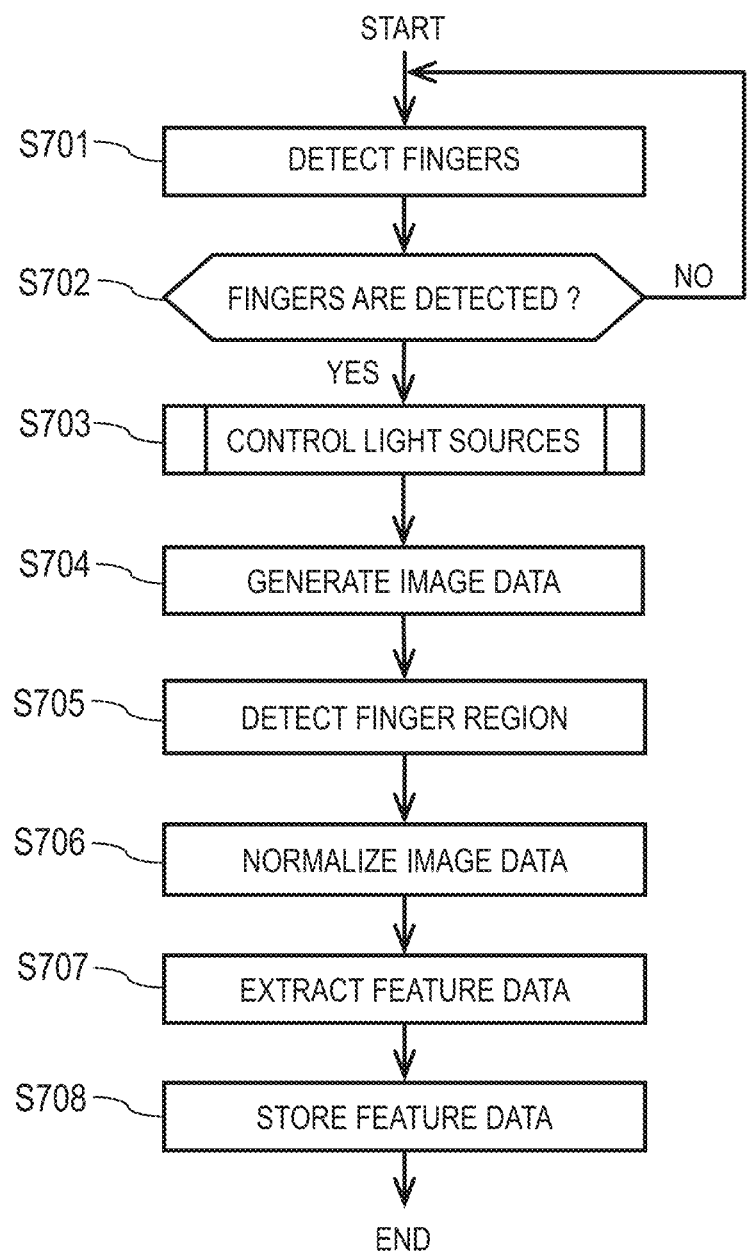
FIG. 7 is a flow chart for illustrating an example of a procedure of registration processing of the finger image data.

FIG. 7 is a flow chart for illustrating an example of a procedure of registration processing of the finger image data. In FIG. 7, an execution subject is the authentication apparatus 108 as an example, but may be the photographing apparatus 100. When the hand 110 is placed over the upper plate portion 100B, the authentication apparatus 108 executes detection of the fingers 111 to 113 (Step S701). Specifically, for example, the imaging unit 101 receives and photoelectrically converts reflected light from the ambient light of the fingers 111 to 113 (or predetermined amounts of irradiation light from the light sources 102) to generate binary image data. Then, the controller 107 separates a main subject and the background of the binary image data, and determines whether a shape of the main subject is the fingers 111 to 113.

In Step S701, the authentication apparatus 108 may take an image while flashing the light sources 102, and execute detection of the fingers 111 to 113 by utilizing a change in luminance of the taken image data. Alternatively, in the case in which the distance sensor 600 is included, the authentication apparatus 108 may detect the existence of the hand 110 that is at a predetermined position or has been brought close to within a certain range with use of the distance sensor 600. Still alternatively, both of the flashing of the light sources 102 and the distance measuring by the distance sensor 600 may be used.

When the fingers 111 to 113 are not detected (Step S702: No), the process returns to Step S701. When the fingers 111 to 113 are detected (Step S702: Yes), the authentication apparatus 108 executes light source control (Step S703). The light source control (Step S703) is processing of controlling the amounts of light of the light sources 102. Details of the light source control (Step S703) are described later with reference to FIG. 9. As a result of being irradiated from the light sources 102 with the amounts of light adjusted in the light source control (Step S703), the imaging unit 101 receives reflected light from the fingers 111 to 113, and generates finger image data by image processing (Step S704). The generated finger image data is stored in the data memory 106 or the storage device 312.

The authentication apparatus 108 detects finger regions from the generated finger image data by image processing (Step S705), and normalizes the finger image data by image processing (Step S706). The normalization is processing of correcting an enlargement ratio and distortion caused by variations in position and variations in posture of the fingers based on positions of the detected fingers. Then, the authentication apparatus 108 extracts feature data of finger blood vessels or fingerprints from the normalized finger image data by image processing (Step S707). The authentication apparatus 108 stores the feature data in the data memory 106 or the storage device 312 (Step S708). In Step S708, the authentication apparatus 108 stores the feature data, but may store the finger image data in the data memory 106 or the storage device 312 without executing the extraction (Step S707) of the feature data.

<Procedure of Authentication Processing of Finger Image Data>

Figure 8:
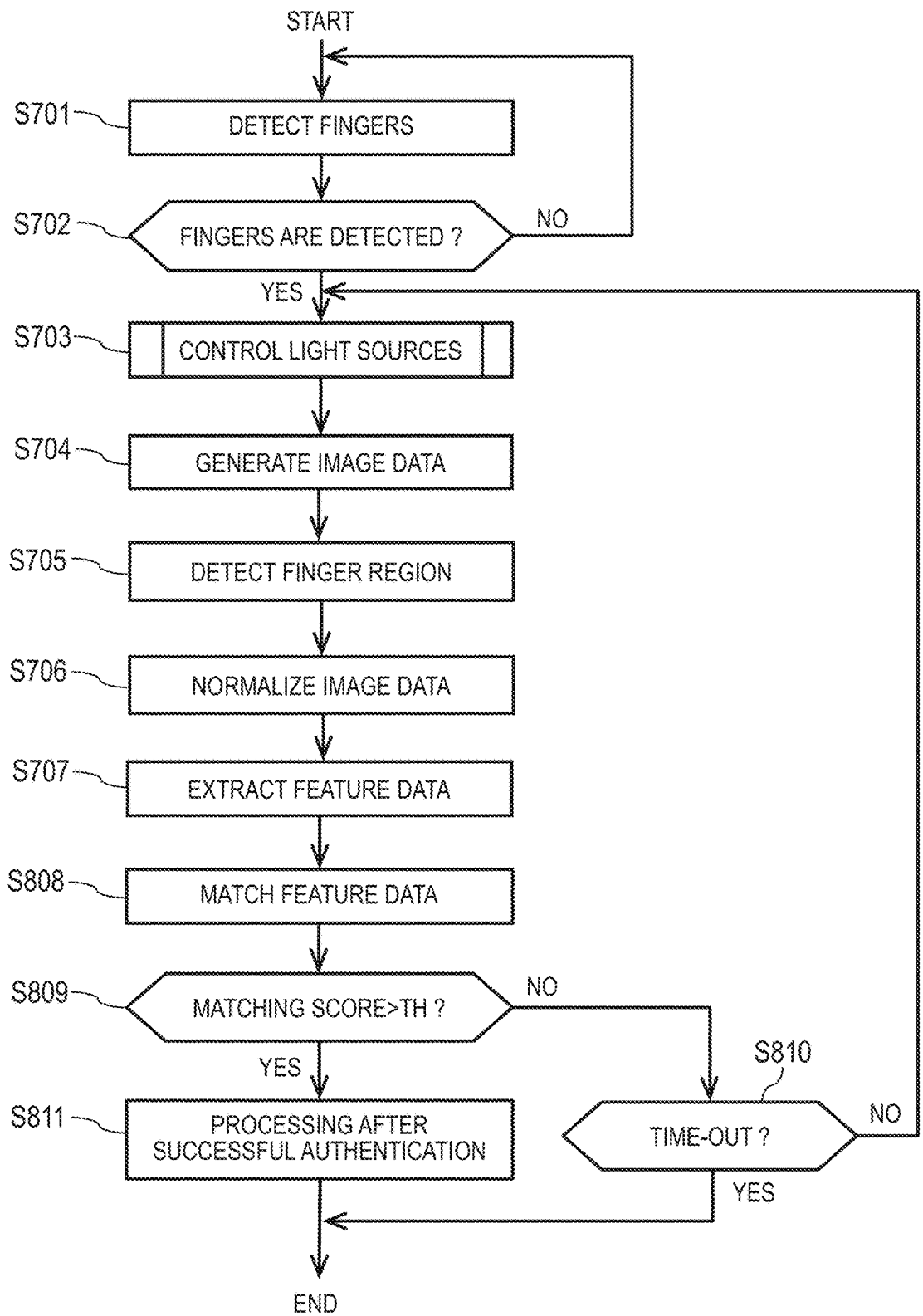
FIG. 8 is a flow chart for illustrating an example of a procedure of authentication processing of the finger image data.

FIG. 8 is a flow chart for illustrating an example of a procedure of authentication processing of the finger image data. In FIG. 8, an execution subject is the authentication apparatus 108 as an example, but may be the photographing apparatus 100. It should be noted, however, that in the case in which the photographing apparatus 100 is the execution subject, Step S808 to Step S811 are executed by the controller 107 or the computer 310 provided on the outside of the photographing apparatus 100. Step S701 to Step S707 are processing steps on fingers as a verification target, but are processing steps common to FIG. 7, and hence description thereof is omitted. Further, in the case in which the finger image data is stored without executing the feature data extraction (Step S707) in FIG. 7, the feature data extraction is executed also on finger image data as a comparison target to be compared with the verification target in Step S707.

After executing Step S707, the authentication apparatus 108 reads the feature data of the comparison target, which has been registered in advance, out of the data memory 106 or the storage device 312, and matches the feature data of the comparison target with feature data of the verification target (Step S808). Specifically, for example, the authentication apparatus 108 calculates a matching score based on the identity of positions of the feature data, and the identity of features.

The identity of positions is, for example, whether there is the feature data of the comparison target at the same position as, or within an allowable range of, a position of the feature data of the verification target. The identity of features is, for example, between the feature data of the verification target and the feature data of the comparison target having the identity of positions, shapes of the blood vessels or the fingerprints shown in the sets of feature data are the same or differences between the shapes are within an allowable range. In the authentication apparatus 108, as the number of sets of feature data that satisfies the identity of positions of the feature data and the identity of features becomes larger, the matching score becomes higher.

Then, the authentication apparatus 108 determines whether the matching score is larger than a threshold TH (Step S809). When the matching score is the threshold TH or smaller (Step S809: No), the authentication apparatus 108 determines whether a time-out has occurred (Step S810). When a time-out period has not elapsed (Step S810: No), the process returns to Step S703. In contrast, when the time-out period has elapsed (Step S810: Yes), the authentication processing ends. Further, in Step S809, when the matching score is larger than the threshold TH (Step S809: Yes), the authentication apparatus 108 executes processing after successful authentication (Step S811), and the authentication processing ends.

<Light Source Control (Step S703)>

Figure 9:
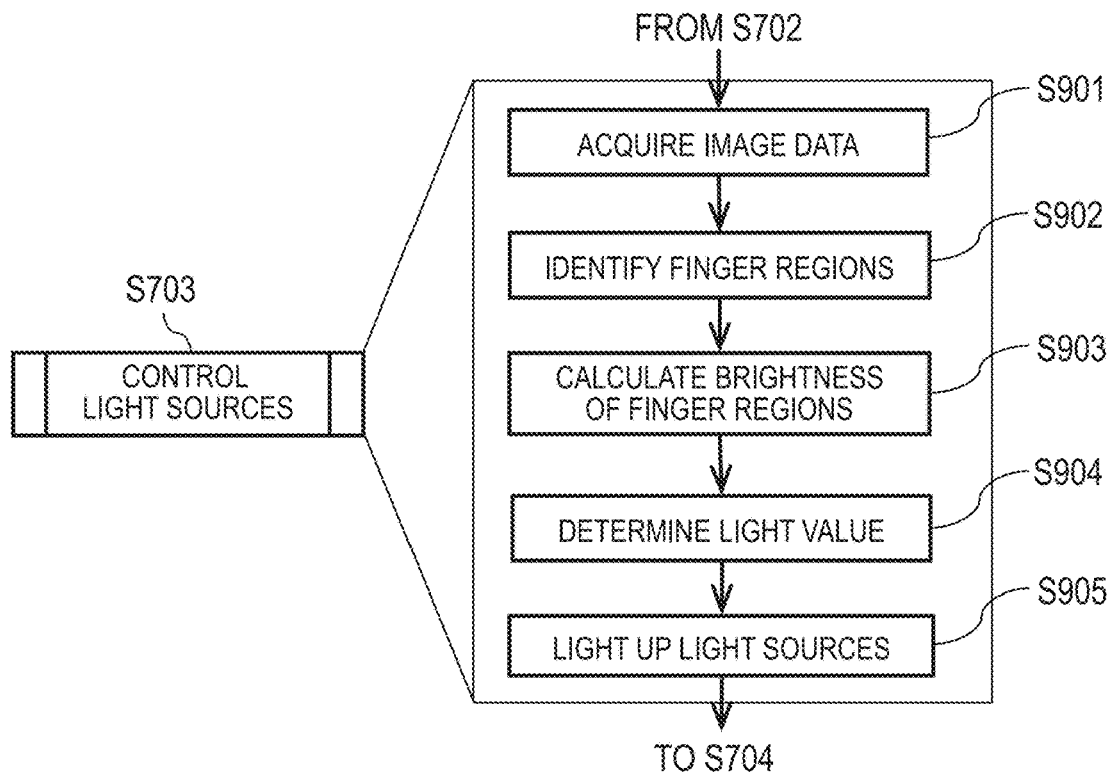
FIG. 9 is a flow chart for illustrating an example of a procedure of detailed processing of the light source control (Step S703) illustrated in FIG. 7 and FIG. 8.

FIG. 9 is a flow chart for illustrating an example of a procedure of detailed processing of the light source control (Step S703) illustrated in FIG. 7 and FIG. 8. After Step S702, the authentication apparatus 108 acquires the image data used in the detection of the fingers 111 to 113 (Step S901), and identifies regions of the plurality of fingers 111 to 113 (Step S902). The authentication apparatus 108 calculates a brightness of the identified finger regions based on luminance information of the finger image data acquired in Step S901 (Step S903). Next, the authentication apparatus 108 determines, based on the brightness of the finger regions calculated in Step S903, a light value of each of the light sources 102 so that the finger regions have an appropriate brightness (Step S904). Then, the authentication apparatus 108 lights up the light source 102 with the light value determined in Step S904 (Step S905), and the process proceeds to Step S704.

The brightness of the finger regions calculated in Step S903 may be, for example, an average brightness value of the finger regions in the finger image data. The average brightness value may be calculated individually for each of the detected fingers 111 to 113, or may be an average of luminance values of all the detected fingers 111 to 113. Further, as the finger regions for which the average brightness value is calculated, as well as using the whole region of the fingers 111 to 113, a local region, for example, an intermediate position between the fingertips and the finger bases, may be used.

Further, in determining the light value in Step S904, the authentication apparatus 108 first sets in advance an appropriate brightness (for example, average luminance) of the finger regions in the image data as a specific target value. Then, the authentication apparatus 108 adjusts the amounts of irradiation light so that the brightness calculated in Step S903 becomes the brightness of the target value, and hence even when the distance D (height) to the fingers 111 to 113 varies, the light sources 102 can irradiate the fingers 111 to 113 with the light having the uniform intensity.

A specific method of determining the light value is a method involving changing the light value one step at a time. Several steps of the light value with which the light sources 102 irradiate are set in advance, and when a brightness of finger regions of image data generated by irradiating with an initial light value is darker than the target value, the authentication apparatus 108 increments the light value by one step. In contrast, when the brightness of the finger regions is brighter than the target value, the authentication apparatus 108 decrements the light value by one step.

Another method of determining the light value is a method utilizing correlation between the light value of the irradiation light from the light sources 102 and the brightness of the finger regions. The authentication apparatus 108 (controller 107) controls, based on a value of a function representing a relationship between the light value and the brightness of the finger regions, the light sources 102 to irradiate at a light value that corresponds to a brightness of the finger regions serving as the target value.

Figure 10:
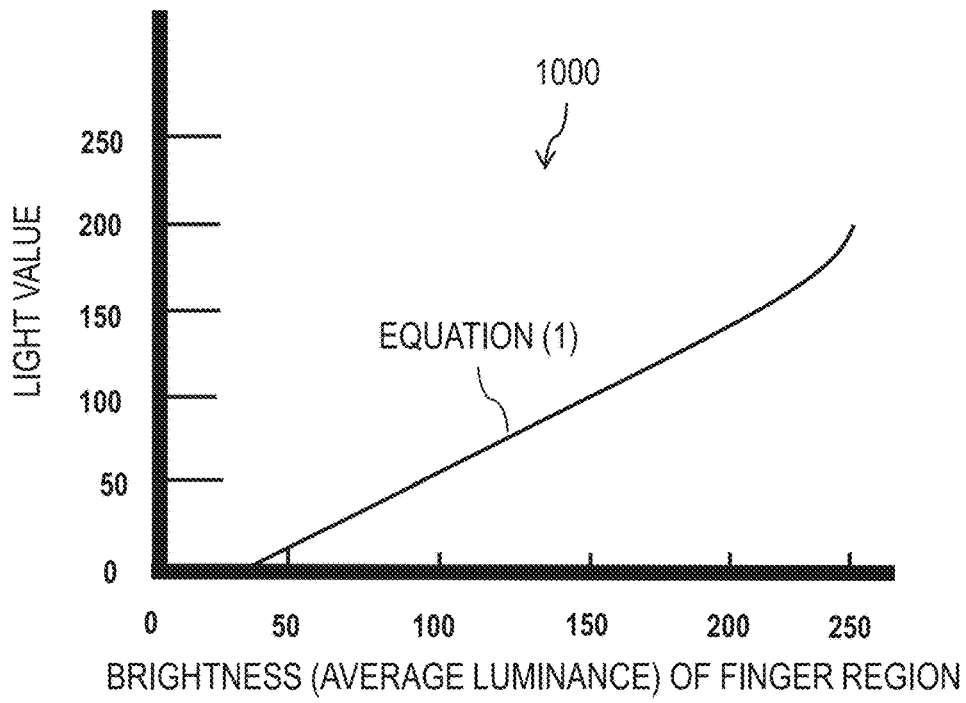
FIG. 10 is a graph for showing an example of a relationship between an amount of irradiation light of a light source and the brightness of the finger regions.

FIG. 10 is a graph for showing an example of a relationship between an amount of irradiation light of a light source 102 and the brightness of the finger regions. A horizontal axis of a graph 1000 is the brightness (for example, average luminance) of the finger regions, and a vertical axis of the graph 1000 is a light value from the light source. Assuming that a relationship between a brightness x of the finger regions and a light value y with which the light sources irradiates can be linearly approximated, the relationship between the brightness x and the light value y can be expressed by Equation (1) below.

$$y = \alpha x + \beta \qquad (1)$$

In Equation (1) above, $\alpha$ and $\beta$ are parameters that are changed depending on the environment and a difference of the fingers, and are determined by calculation every time the brightness x of the finger regions is calculated. After the function of Equation (1) is determined, the authentication apparatus 108 substitutes a target brightness x' of the finger regions into Equation (1) above to determine a light value y' that corresponds to the brightness x', and lights up the light sources 102 at the light value y'.

In FIG. 10, the case in which the relationship between the light value and the brightness of the finger regions can be linearly approximated has been described as an example, but the amount of light can be controlled similarly even in a case in which the relationship cannot be linearly approximated (the relationship is non-linear).

Figure 11:
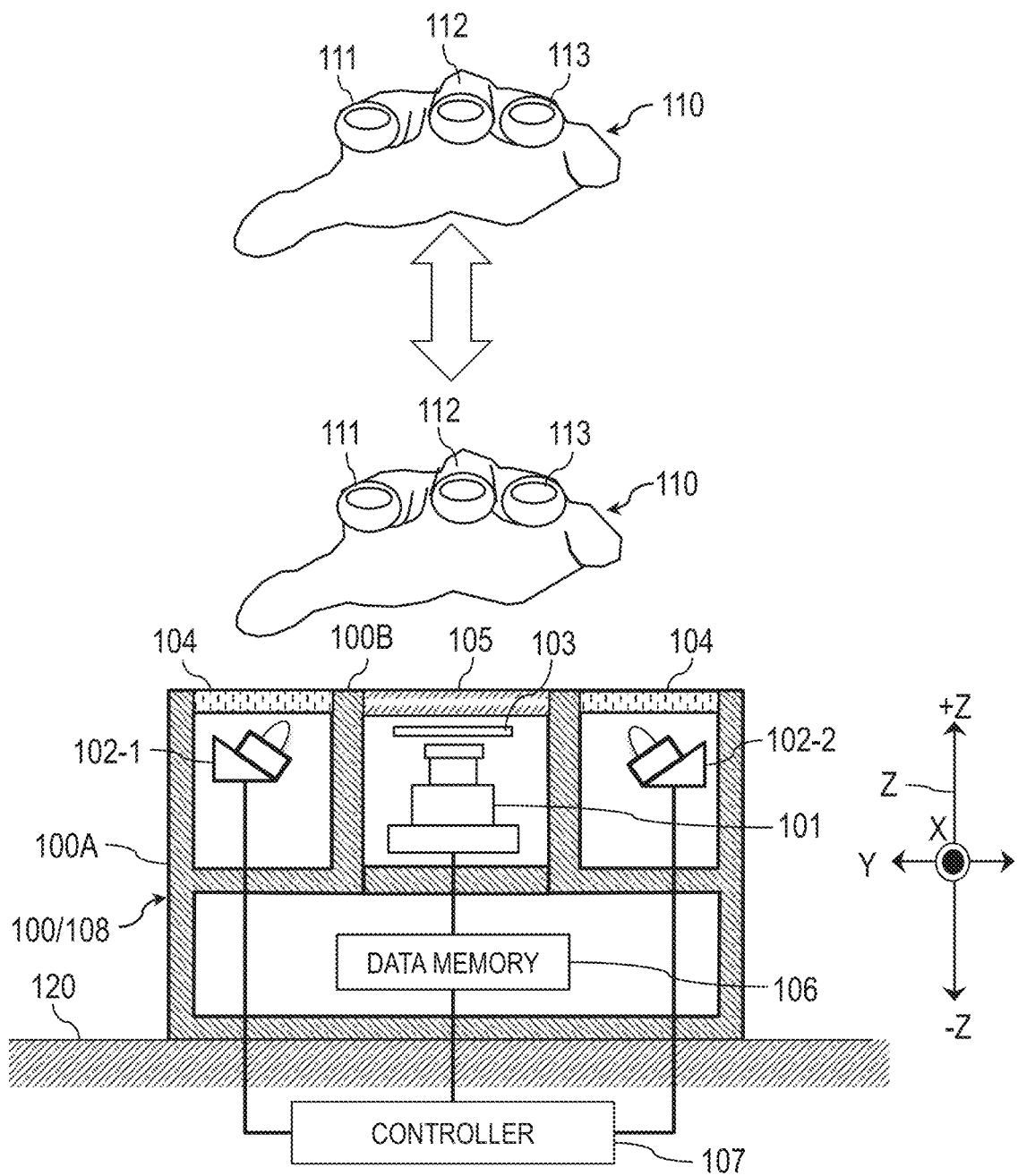
FIG. 11 is an explanatory diagram for illustrating a change in position of the hand 110 with respect to the photographing apparatus and the authentication apparatus.

FIG. 11 is an explanatory diagram for illustrating a change in position of the hand 110 with respect to the photographing apparatus 100 and the authentication apparatus 108. In a case in which a constant amount of light is irradiated from the light sources 102, when the height in a Z-axis direction of the hand 110 presented by the user varies, an amount of light with which the fingers 111 to 113 are irradiated changes depending on the distance in a Z direction between the hand 110 and the light sources 102, and excess and deficiency of an amount of reflected light from the fingers 111 to 113 occur. As a result, the brightness of the finger region may differ for each of the fingers 111 to 113, and there is a fear in that stable finger image data cannot be generated. In the case in which the distance sensor 600 can be used, the authentication apparatus 108 can control the amounts of irradiation light of the light sources 102 depending on the measured distance D to irradiate the fingers 111 to 113 with the light always having the uniform intensity. In other words, the authentication apparatus 108 controls the amounts of light from the light sources 102 to be increased or reduced depending on the distance D. For example, the authentication apparatus 108 reduces the amounts of light from the light sources 102 as the distance D becomes shorter, and increases the amounts of light from the light sources 102 as the distance D becomes longer.

<Examples of Adjusting Amounts of Light Depending on Variation in Posture of Hand 110>

Figure 12:
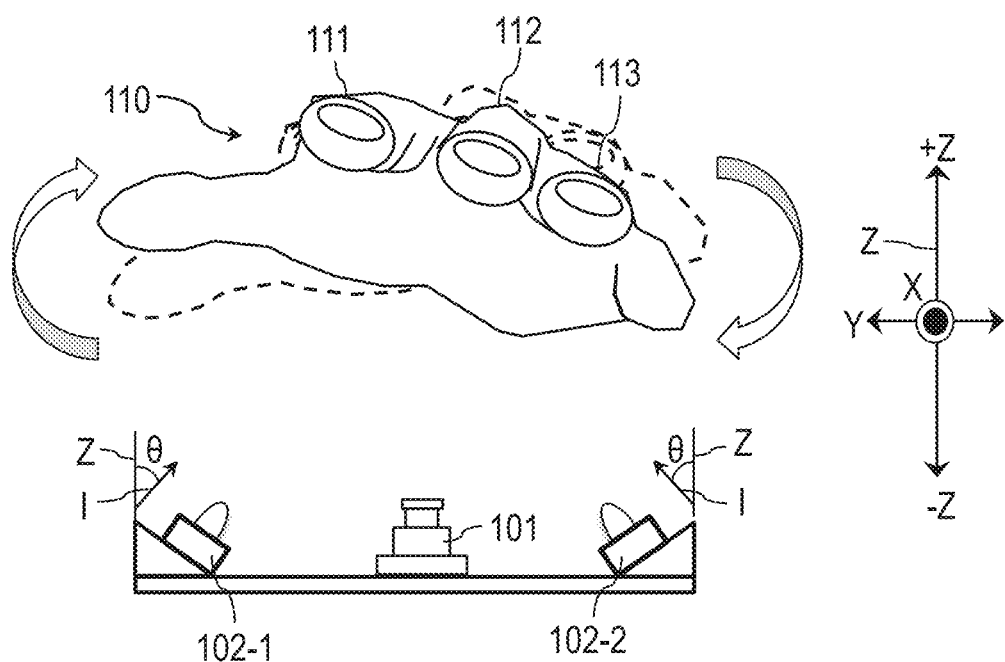
FIG. 12 is an explanatory diagram for illustrating Example 1 of adjusting the amounts of light depending on a variation in posture of the hand.

FIG. 12 is an explanatory diagram for illustrating Example 1 of adjusting the amounts of light depending on a variation in posture of the hand 110. FIG. 12 shows a state in which the hand 110 is rotated about the X axis. The rotation about the X axis is a roll (rotation). Due to variations in posture of the fingers caused by the roll rotation, heights in the Z-axis direction of the index finger 111, the middle finger 112, and the third finger 113 as the subject are different.

In that case, the controller 107 can uniformalize brightnesses of all the finger regions to generate finger image data by changing amounts of irradiation light of the light sources 102-1 and 102-2. For example, the controller 107 determines the amount of irradiation light of the light source 102-1 based on a brightness of a finger region of the index finger 111 in the generated finger image data, and determines the amount of irradiation light of the light source 102-2 based on a brightness of a finger region of the third finger 113. In this manner, the controller 107 determines the amount of irradiation light for each of the light sources 102-1 and 102-2 based on a brightness of the finger at the shortest distance. Accordingly, in the case of the roll rotation as in FIG. 12, the controller 107 controls the light source 102-1 to irradiate a larger amount of light than the light source 102-2, to thereby photograph the whole fingers with a uniform brightness by the imaging unit 101.

Alternatively, the controller 107 may adjust the amount of light of the light sources 102-1 and 102-2 based on brightnesses of finger regions including not only the index finger 111 and the third finger 113 but also the middle finger 112. Without limiting to the middle finger 112, the brightnesses of all the fingers 111 to 113 are affected by the irradiation light of both of the light sources 102-1 and 102-2. Thus, considering for each of the fingers 111 to 113 the effects of the amounts of irradiation light of the light sources 102-1 and 102-2 on the brightness of the finger region, the controller 107 can determine optimum amounts of irradiation light of the light sources 102-1 and 102-2 so that all the fingers 111 to 113 have a uniform brightness.

Figure 13:
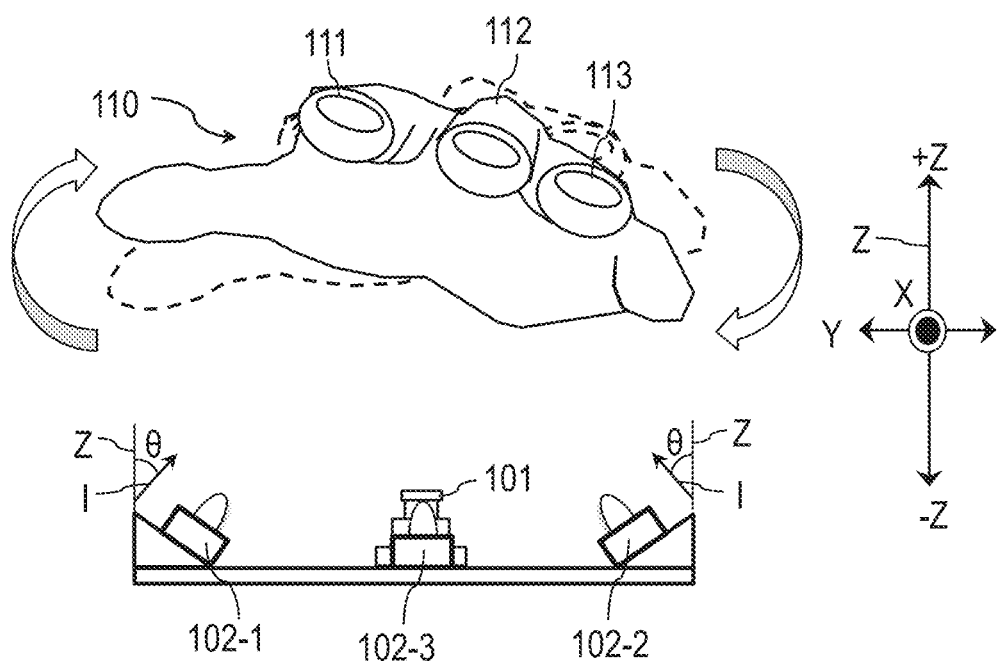
FIG. 13 is an explanatory diagram for illustrating Example 2 of adjusting the amounts of light depending on a variation in posture of the hand.

FIG. 13 is an explanatory diagram for illustrating Example 2 of adjusting the amounts of light depending on a variation in posture of the hand 110. A difference from FIG. 12 is that a light source 102-3 is provided between the light sources 102-1 and 102-2. An optical axis of the light source 102-3 is not I, but is the Z axis. With this configuration, the index finger 111 corresponds to the light source 102-1, the third finger 113 corresponds to the light source 102-2, and the middle finger 112 corresponds to the light source 102-3.

For example, the controller 107 determines the amount of irradiation light of the light source 102-1 based on a brightness of a finger region of the index finger 111, determines the amount of irradiation light of the light source 102-2 based on a brightness of a finger region of the third finger 113, and determines an amount of irradiation light of the light source 102-3 based on a brightness of a finger region of the middle finger 112. In this manner, the controller 107 determines the amount of irradiation light for each of the light sources 102-1 to 102-3 based on the brightness of the finger at the shortest distance. Accordingly, in the case of the roll rotation as in FIG. 13, the controller 107 controls the light source 102-1 to irradiate a larger amount of light than the light sources 102-2 and 102-3, and controls the light source 102-3 to irradiate a larger amount of light than the light source 102-2, to thereby photograph the whole fingers with a uniform brightness by the imaging unit 101.

As described above, the controller 107 can generate clear finger image data more robustly against the variations in position and the variations in posture of the fingers 111 to 113 by adjusting the amounts of irradiation light from the light sources 102 corresponding to the respective fingers. Further, in the apparatus configurations of FIG. 12 and FIG. 13, although not shown, each of the light sources 102-1 to 102-3 may be arranged in plurality along the X direction.

Second Embodiment

A second embodiment of this invention is an example in which, in the first embodiment, light sources 102 are further arrayed in the X-axis direction. The same components as those in the first embodiment are denoted by the same reference symbols, and description thereof is omitted.

Figure 14:
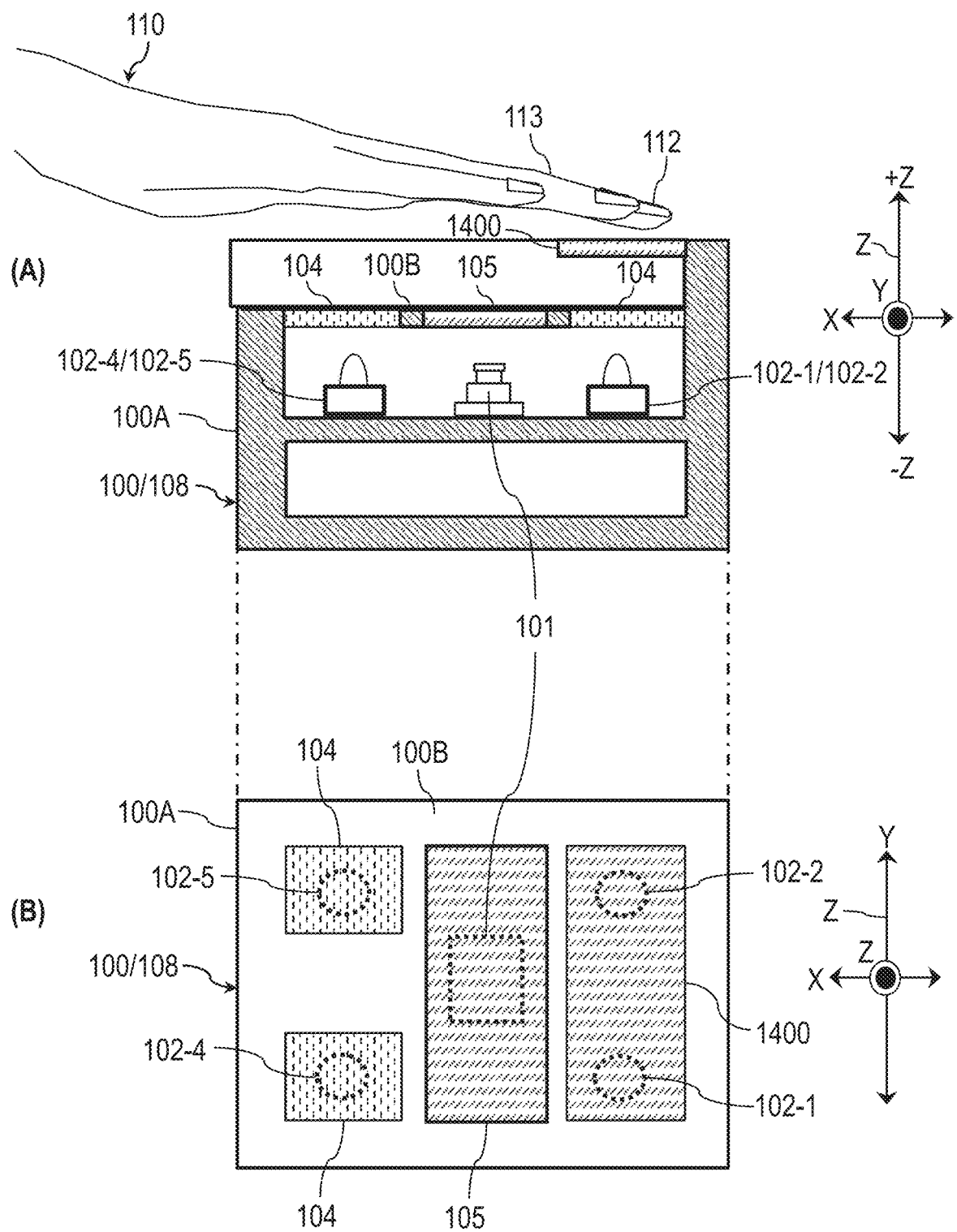
FIG. 14 is an explanatory diagram for illustrating Configuration Example 1 of a photographing apparatus and an authentication apparatus according to the second embodiment.

FIG. 14 is an explanatory diagram for illustrating Configuration Example 1 of a photographing apparatus 100 and an authentication apparatus 108 according to the second embodiment. Part (A) is a side sectional view of the photographing apparatus 100 and the authentication apparatus 108, and Part (B) is a plan view of the photographing apparatus 100 and the authentication apparatus 108.

Light sources 102-1 and 102-4 corresponding to the index finger 111 are arrayed in the X direction. For example, the light source 102-1 is provided at a position corresponding to the fingertip of the index finger 111, and the light source 102-4 is provided at a position corresponding to the base of the index finger 111. An optical axis I of the light source 102-4 is, as with the light source 102-1, a direction inclined about the X axis by a predetermined angle θ from the Z axis toward a direction in which the other light source 102-5 exists.

Light sources 102-2 and 102-5 corresponding to the third finger 113 are arrayed in the X direction. For example, the light source 102-2 is provided at a position corresponding to the fingertip of the third finger 113, and the light source 102-5 is provided at a position corresponding to the base of the third finger 113. An optical axis I of the light source 102-5 is, as with the light source 102-2, a direction inclined about the X axis by a predetermined angle θ from the Z axis toward a direction in which the other light source 102-4 exists.

In the +Z direction from the second optical filter 104 corresponding to the light sources 102-1 and 102-4, a fingertip presentation plate 1400 is provided to the housing 100A in parallel to the X axis. The fingertip presentation plate 1400 is a transparent plate-like member made of, for example, acryl or glass, and the fingers 111 to 113 can be placed thereon. With this configuration, positions of the fingertips of the hand 110 presented by the user can be guided to the fingertip presentation plate 1400. Thus, even in a case in which the fingers are placed on, or contactlessly placed over, the fingertip presentation plate 1400, the whole fingers can be photographed by an imaging unit 101.

In the vicinity of the contour of side surfaces in the array direction Y of each of the fingers 111 to 113, an amount of reflected light of irradiation light of the light sources 102 becomes easily deficient. The vicinity of the contour of the fingertip has a stereoscopic shape with many curved surfaces, and easily becomes deficient in amount of reflected light of the irradiation light of the light sources 102, and the vicinity of the fingertip tends to be significantly dark in the finger image data. To address this problem, through provision of the light sources 102-4 and 102-5 corresponding to the finger bases, the light sources 102-4 and 102-5 and the light sources 102-1 and 102-2 irradiate different amounts of irradiation light. Specifically, for example, the light sources 102-1 and 102-2 irradiate a larger amount of light than the light sources 102-4 and 102-5. As a result, the imaging unit 101 can photograph the whole fingers 111 to 113 with an appropriate brightness.

The light sources 102-1 and 102-2 and the light sources 102-4 and 102-5 may irradiate preset amounts of light. Further, the set light values may be individually adjustable.

Further, as in the first embodiment, in the case in which the authentication apparatus 108 generates and authenticates image data of multiple modalities such as the blood vessels and the fingerprints by using light having a plurality of different wavelengths for the plurality of light sources 102, the authentication apparatus 108 may adjust the amounts of irradiation light of the light sources 102-1 and 102-2 and amounts of irradiation light of the light sources 102-4 and 102-5 to amounts of irradiation light suitable for the modalities in which images are to be taken, respectively.

For example, for a region on a base side of the fingers 111 to 113, the authentication apparatus 108 may control the amounts of irradiation light of the near-infrared light of the light sources 102-1 and 102-2 so as to photograph the blood vessels, and for a region on a fingertip side, the authentication apparatus 108 may control the amounts of irradiation light of visible light of the light sources 102-4 and 102-5 so as to photograph the fingerprints.

Figure 15:
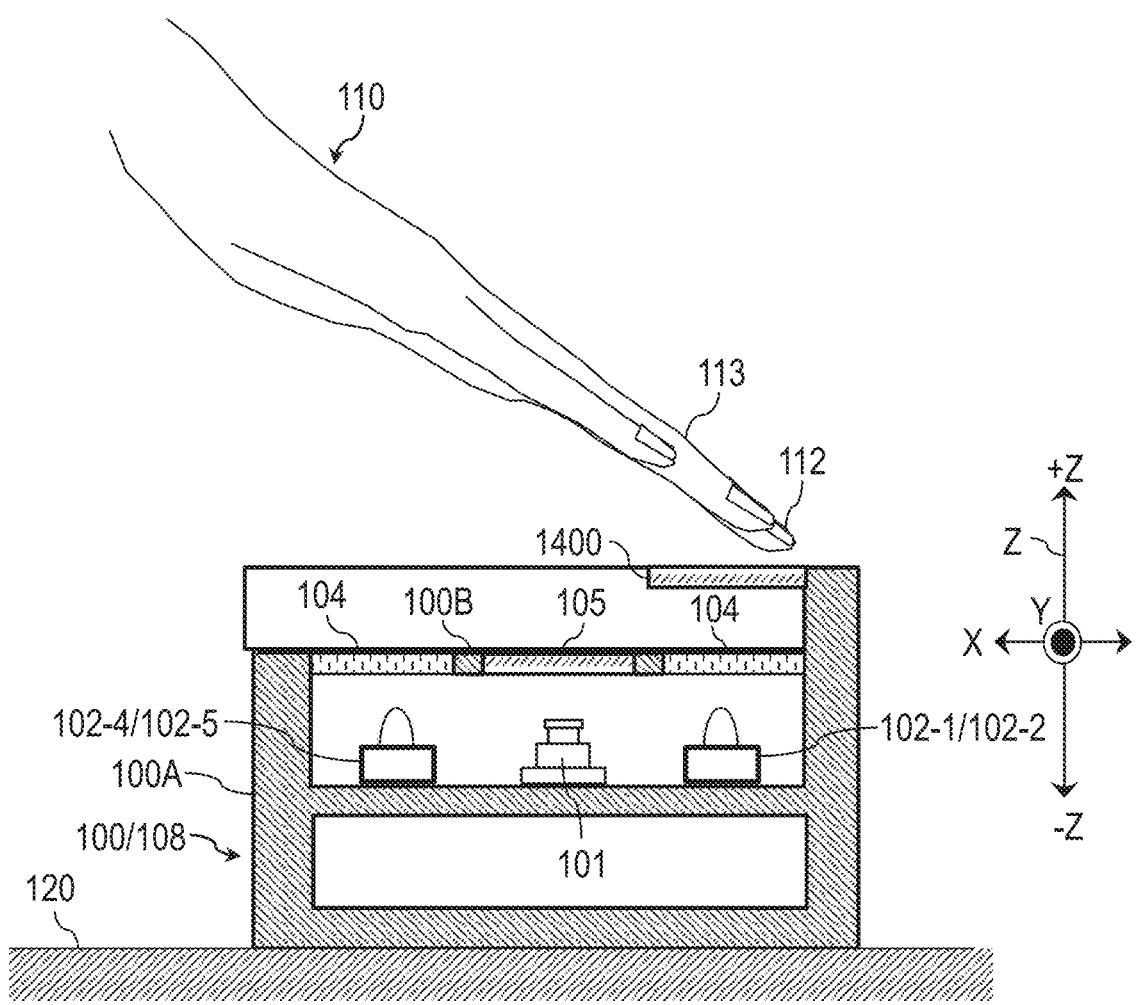
FIG. 15 is an explanatory diagram for illustrating an example of controlling, in Configuration Example 1 of the photographing apparatus and the authentication apparatus according to the second embodiment, amounts of light depending on a variation in posture of the fingers.

FIG. 15 is an explanatory diagram for illustrating an example of controlling, in Configuration Example 1 of the photographing apparatus 100 and the authentication apparatus 108 according to the second embodiment, amounts of light depending on a variation in posture of the fingers 111 to 113. As illustrated in FIG. 15, in a posture in which the fingertips are lowered in a −Z-axis direction further than the finger bases, when the light sources 102-1 and 102-2 and the light sources 102-4 and 102-5 irradiate the same amount of light, the irradiation light attenuates in intensity depending on the distance. Accordingly, an amount of light to irradiate a finger base side is reduced with respect to a fingertip side, and the finger base side becomes relatively darker in the finger image data. Consequently, as compared to the case in which postures of the fingers 111 to 113 are parallel to the X-axis direction, clear finger image data is not generated.

To address this problem, the controller 107 adjusts the amounts of light individually for the light sources 102-4 and 102-5 which irradiate the finger base side and for the light sources 102-1 and 102-2 which irradiate the fingertip side. As a result, as in the case in which the postures of the fingers 111 to 113 are parallel to the X-axis direction, clear finger image data is generated.

As a method of adjusting the amounts of light, the controller 107 adjusts the amounts of light of the light sources 102-1 and 102-2 by using a distance D measured by a distance sensor 600 provided for each of the light sources 102. For example, the controller 107 controls the amounts of irradiation light from the light sources 102 to be increased or reduced so that the amount of light of the light source 102 with the longer distance D becomes larger than the amount of light of the light source 102 with the shorter distance D.

Further, the controller 107 adjusts the amounts of light of the light sources 102-4 and 102-5 based on brightnesses of finger regions on the finger base side in the generated finger image data, and adjusts the amounts of light of the light sources 102-1 and 102-2 based on brightnesses of finger regions on the fingertip side in the generated finger image data. In controlling the amounts of light based on the brightnesses of the finger regions, irradiation light from the light sources 102-1 and 102-2 and irradiation light from the light sources 102-4 and 102-5 may overlap in a part of the finger regions. When the brightnesses of the finger regions are affected as described above, the controller 107 may determine light values of the light sources 102-1 and 102-2 and the light sources 102-4 and 102-5 so that the following three regions: the finger base region, the fingertip region, and the overlapping region of the irradiation light from the light sources 102-1 and 102-2 and the irradiation light from the light sources 102-4 and 102-5 have a uniform brightness.

Figure 16:
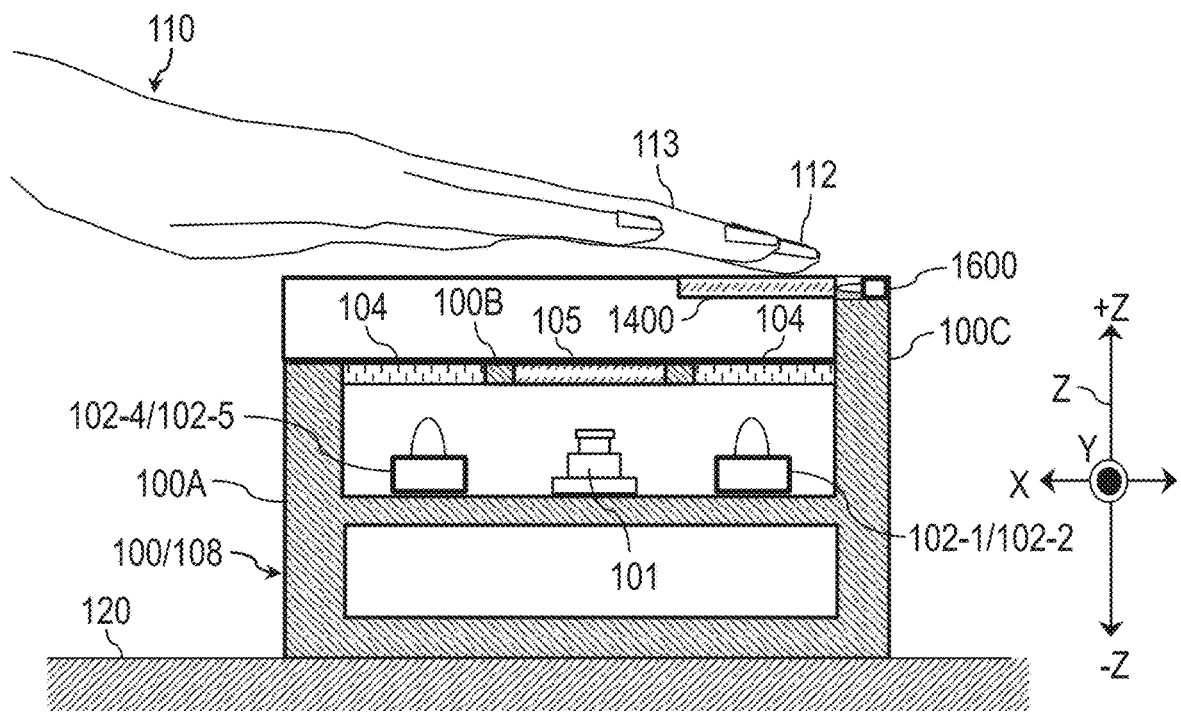
FIG. 16 is an explanatory diagram for illustrating Configuration Example 2 of the photographing apparatus and the authentication apparatus according to the second embodiment.

FIG. 16 is an explanatory diagram for illustrating Configuration Example 2 of the photographing apparatus 100 and the authentication apparatus 108 according to the second embodiment. A difference from Configuration Example 1 of FIG. 14 is that, in a +Z-side end portion of a front plate portion 100C of the housing 100A, a light source 1600 is provided at a position opposed to a side surface of the fingertip presentation plate 1400. Irradiation light from the light source 1600 enters from the side surface of the fingertip presentation plate 1400.

When the user brings the fingertips into contact with, or places fingertips over, the fingertip presentation plate 1400, and the authentication apparatus 108 executes the authentication processing, under a state in which light is irradiated from the light source 1600, the imaging unit 101 photographs fingerprints of the fingertips that are in contact with the fingertip presentation plate 1400.

Specifically, for example, the light that has entered the fingertip presentation plate 1400 from the light source 1600 propagates while being totally reflected by a boundary between the fingertip presentation plate 1400 and air. At this time, when the user touches the fingertip presentation plate 1400 with the fingertips, in ridge portions being convex portions of the fingerprints of the fingertips that are in touch, a refractive index between moisture on the surface of the fingertip and the fingertip presentation plate 1400 becomes larger than a refractive index of air. Thus, a total reflection condition is not satisfied any more, and the light from the light source 1600 is scattered.

For that reason, the ridge portions of the fingerprints of the fingertips are dark, but the other regions are bright. The imaging unit 101 can photograph such fingerprints, and the controller 107 can generate image data of the fingerprints. As described above, the controller 107 can execute generation of image data of blood vessels and image data of the skin surface (back side of fingers) near the finger bases by the light sources 102-4 and 102-5, and generation of image data of fingerprints by the light source 1600. As described above, the controller 107 can acquire a plurality of types of biometric information on one user in one authentication process, and hence highly accurate authentication can be achieved without compromising convenience.

Figure 17:
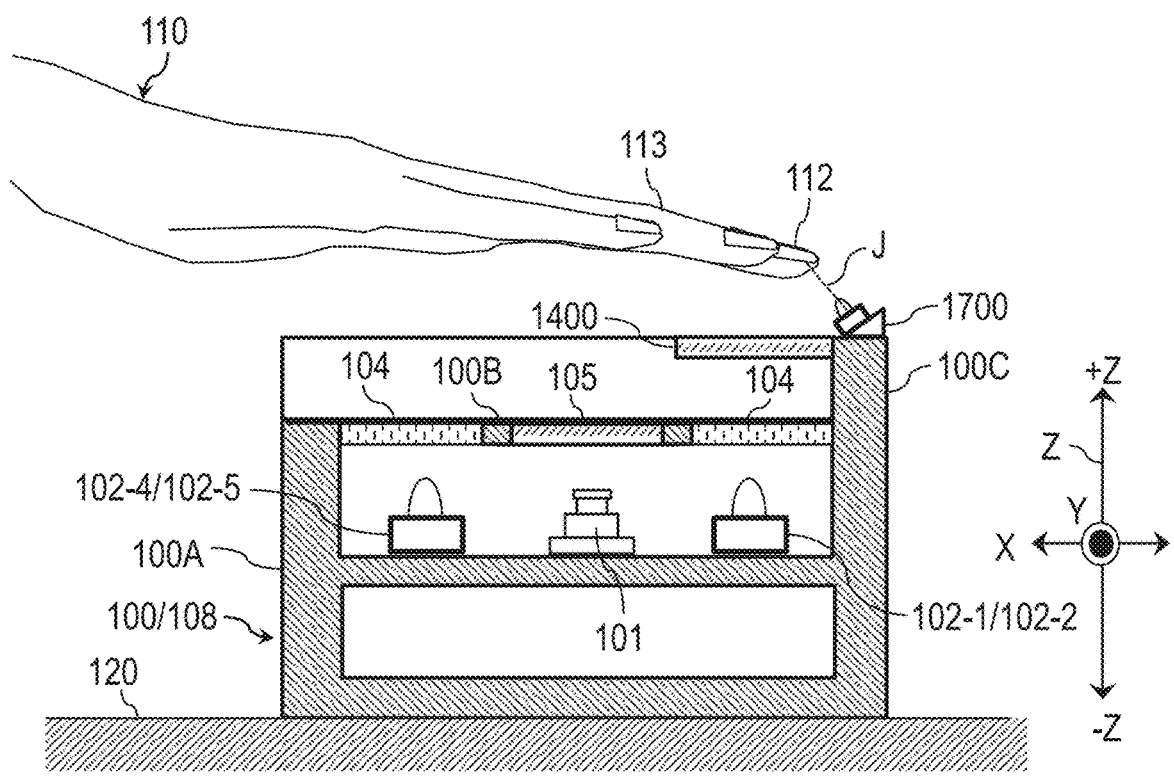
FIG. 17 is an explanatory diagram for illustrating Configuration Example 3 of the photographing apparatus and the authentication apparatus according to the second embodiment.

FIG. 17 is an explanatory diagram for illustrating Configuration Example 3 of the photographing apparatus 100 and the authentication apparatus 108 according to the second embodiment. A difference from Configuration Example 1 of FIG. 14 is that a light source 1700 is provided on a +Z-side end surface of the front plate portion 100C of the housing 100A, which is flush with the fingertip presentation plate 1400. An optical axis J of the light source 1700 is a direction inclined about the Y axis from the Z axis toward the fingertip presentation plate 1400 side. With this configuration, the light source 1700 can irradiate light toward the fingertips presented on the fingertip presentation plate 1400.

Light from the light sources 102-1 and 102-2 is transmitted through the fingertip presentation plate 1400 and irradiates the fingertips. Even in a case in which, when the light is transmitted through the fingertip presentation plate 1400, an amount of light is significantly attenuated, and the fingertips are not irradiated with a sufficient amount of light, with irradiation light from the light source 1700, the vicinity of the contour of each of the fingertips is more likely to be irradiated with the irradiation light. Consequently, the controller 107 can generate clear image data of the blood vessels of the whole finger regions.

In a case in which the irradiation light from the light sources 102-1 and 102-2 is scattered or specular reflection occurs in the housing 100A due to the fingertip presentation plate 1400, and effects of noise are significant, the controller 107 may photograph the fingertips by the imaging unit 101 by reducing an amount of the irradiation light from the light source 1700 instead of increasing the amounts of irradiation light from the light sources 102-1 and 102-2.

In FIG. 17, the light source 1700 is arranged at a position in the +Z direction of the fingertip presentation plate 1400, but the light source 1700 may be arranged at a position in the −Z direction of the fingertip presentation plate 1400. In this case, the irradiation light from the light source 1700 is transmitted through the fingertip presentation plate 1400 to irradiate the fingertips. With this configuration, a height in the Z-axis direction of the housing 100A can be reduced, and hence further downsizing can be achieved as compared to the configuration illustrated in FIG. 17. The example in which the fingertip presentation plate 1400 is provided has been described in the second embodiment, but it should be understood that similar effects can be obtained even in a case in which the fingertip presentation plate 1400 is not provided.

Third Embodiment

A third embodiment of this invention is an example in which, in the first embodiment and the second embodiment, auxiliary light sources are provided on inner surfaces of the housing 100A. Through provision of the auxiliary light sources, the controller 107 detects contours of the fingers stably. The same components as those in the first embodiment and the second embodiment are denoted by the same reference symbols, and description thereof is omitted.

Figure 18:
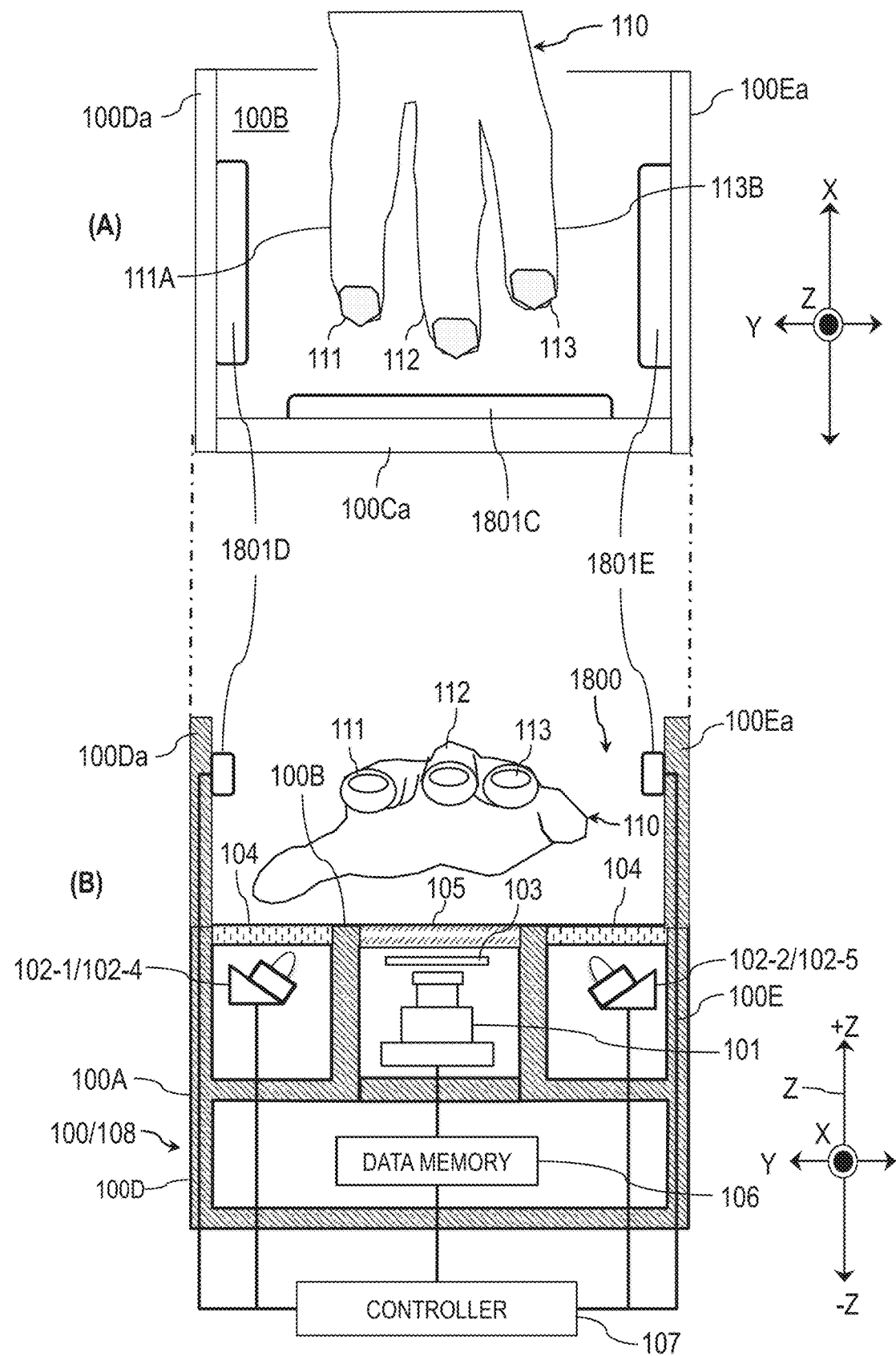
FIG. 18 is an explanatory diagram for illustrating a configuration example of a photographing apparatus and an authentication apparatus according to the third embodiment.

FIG. 18 is an explanatory diagram for illustrating a configuration example of a photographing apparatus 100 and an authentication apparatus 108 according to the third embodiment. Part (A) is a plan view of the photographing apparatus 100 and the authentication apparatus 108, and Part (B) is a sectional view of the photographing apparatus 100 and the authentication apparatus 108. The front plate portion 100C, a first side plate portion 100D, and a second side plate portion 100E protrude in the +Z direction from the upper plate portion 100B. Those protruding portions are referred to as a front protruding end 100Ca of the front plate portion 100C, a first side protruding end 100Da of the first side plate portion 100D, and a second side protruding end 100Ea of the second side plate portion 100E. In a space 1800 outside the housing 100A, which is surrounded by the front protruding end 100Ca, the first side protruding end 100Da, the second side protruding end 100Ea, and the upper plate portion 100B, the hand 110 of the user is presented.

An auxiliary light source 1801C is provided on an inner wall surface of the front protruding end 100Ca. An auxiliary light source 1801D is provided on an inner wall surface of the first side protruding end 100Da. An auxiliary light source 1801E is provided on an inner wall surface of the second side protruding end 100Ea. The auxiliary light source 1801C is a light source along the Y-axis direction, and the auxiliary light sources 1801D and 1801E are light sources along the X-axis direction. The auxiliary light sources 1801C, 1801D, and 1801E are coupled to the controller 107. The auxiliary light sources 1801C, 1801D, and 1801E are simply referred to as the auxiliary light sources 1801 when no distinction is made thereamong.

The auxiliary light sources 1801C, 1801D, and 1801E surround the fingers 111 to 113 presented into the space 1800. With this configuration, the auxiliary light source 1801C irradiates light along the Y-axis direction toward the fingertips of the index finger 111, the middle finger 112, and the third finger 113, and between the fingers. The auxiliary light source 1801D irradiates light along the X-axis direction toward a side surface of the index finger 111. The auxiliary light source 1801E irradiates light along the X-axis direction toward a side surface of the third finger 113. In this manner, the vicinity of the contours of the fingers is irradiated with irradiation light from the auxiliary light sources 1801. Assuming a case in which the user presents the fingers to the authentication apparatus 108 contactlessly, the auxiliary light sources 1801 may be arranged further in the +Z direction.

As described above, even in a case in which the brightnesses near the finger contours are insufficient, through application of the irradiation light from the auxiliary light sources 1801, an imaging unit 101 can receive reflected light having a sufficient brightness, and the fingers can be detected stably and with high accuracy.

Wavelengths of the irradiation light from the auxiliary light sources 1801 may be the same wavelengths as the irradiation light of the light sources 102. With this configuration, bright image data of the blood vessels over the whole finger regions is easily generated. Alternatively, the wavelengths of the irradiation light from the auxiliary light sources 1801 may be different from the wavelengths of the light sources 102. By setting the wavelengths of the irradiation light from the auxiliary light sources 1801 to wavelengths hardly included in the ambient light, the background region and the finger regions can be more differentiated, and the accuracy of detecting the fingers can be increased.

Further, in the case in which light of a plurality of wavelengths, that is, near-infrared light and visible light, are used for the plurality of light sources 102, and fingers are detected from finger image data obtained by irradiating the fingers with the visible light, the wavelengths of the auxiliary light sources 1801 may be the same wavelengths as the visible light of the light sources 102. With this configuration, contour lines of the fingers can be detected stably by the color of the irradiation light.

Further, in a stand-by state before the authentication processing, the controller 107 may control the auxiliary light sources 1801 to irradiate visible light having a different wavelength from the light sources 102. With this configuration, the fact that the authentication apparatus 108 is in the stand-by state can be visually checked.

When the user presents his or her fingers into the space 1800, and the controller 107 detects the fingers (Step S702: Yes), the controller 107 switches the wavelength of the irradiation light from the auxiliary light sources 1801 to the same wavelength as the light sources 102 to irradiate visible light, and executes the authentication processing (authentication state). The light sources 102 and the auxiliary light sources 1801 irradiate the visible light having the same wavelength, and hence the controller 107 can photograph the whole finger regions brightly. Further, the wavelength of the irradiation light from the auxiliary light sources 1801 is changed, and hence the user can visually check that the authentication apparatus 108 has transitioned from the stand-by state to the authentication state.

In the case in which only one wavelength is used as the wavelength of the irradiation light from the auxiliary light sources 1801, the controller 107 may change amounts of irradiated light between the stand-by state and the authentication state, or may indicate the transition of the state by changing lighting pattern of the auxiliary light sources 1801 from a flashing state to always lit. The controller 107 controls the auxiliary light sources 1801 so that, when the authentication is successful or when the authentication is unsuccessful, the lighting pattern is changed, for example, light is irradiated with a different wavelength or in a different amount from the stand-by state and the authentication state, or the light is turned off. In this manner, the controller 107 can notify the user of the authentication result.

Further, the photographing apparatus 100 and the authentication apparatus 108 according to the first embodiment and the second embodiment described above may be configured as in the following items (1) to (15).

(1) For example, the above-mentioned photographing apparatus 100 includes: an imaging unit 101 which is arranged at a position opposed to a plurality of fingers 111 to 113 to be presented, and is configured to image the plurality of fingers 111 to 113; and a plurality of light sources 102 which are arranged in plurality in an array direction of the plurality of fingers 111 to 113, and are configured to irradiate the plurality of fingers 111 to 113 with light from an outside of an opposing region 130 in which the imaging unit 101 is opposed to the plurality of fingers 111 to 113 toward an inside of the opposing region 130. With this configuration, the light sources 102 can irradiate not only the back surfaces of the fingers 111 to 113 but also the side surfaces of the fingers 111 to 113 with light, and inhibit places in which an insufficient amount of light occurs. In other words, unevenness in amount of light over the plurality of fingers 111 to 113 can be inhibited.

(2) Further, in the photographing apparatus 100 according to Item (1), the plurality of light sources 102 may be arranged in plurality in an array direction Y of the plurality of fingers 111 to 113, and may be arranged in plurality in a longitudinal direction X of the plurality of fingers 111 to 113. With this configuration, the light sources 102 can irradiate light from the fingertips to the bases of the fingers 111 to 113.

(3) Further, in the photographing apparatus 100 according to Item (2), a first amount of irradiation light from first light sources (102-1, 102-2) and a second amount of irradiation light from second light sources (102-4, 102-5) are different, the first light sources being arranged in the longitudinal direction of the plurality of fingers 111 to 113, the second light sources being arranged in the longitudinal direction of the plurality of fingers 111 to 113 and closer to a base side of the plurality of fingers 111 to 113 than the first light sources are. With this configuration, the amounts of irradiation light can be changed depending on the irradiation position on the fingers 111 to 113.

(4) Further, in the photographing apparatus 100 according to Item (3), the first amount of irradiation light is larger than the second amount of irradiation light. With this configuration, an insufficient amount of light on the fingertip side can be inhibited, and the amounts of light can be uniformalized over the fingers 111 to 113.

(5) Further, in the photographing apparatus 100 according to Item (1), the plurality of light sources 102 are arranged so that first distances to a closest finger of the plurality of fingers 111 to 113 are the same or a difference between the first distances is within a first tolerance range, and so that second distances to a farthest finger of the plurality of fingers 111 to 113 are the same or a difference between the second distances is within a second tolerance range. With this configuration, the amounts of light can be uniformalized over the fingers 111 to 113.

(6) Further, in the photographing apparatus 100 according to Item (1), the plurality of light sources 102 include a light source configured to irradiate visible light. With this configuration, the patterns (fingerprints) of the back surfaces of the fingers 111 to 113 can be photographed.

(7) Further, in the photographing apparatus 100 according to Item (1), the plurality of light sources 102 include a light source configured to irradiate near-infrared light. With this configuration, the blood vessels of the fingers 111 to 113 can be photographed.

(8) Further, in the photographing apparatus 100 according to Item (1), at least one of the plurality of light sources 102 includes a second optical filter 104 configured to pass light having a particular wavelength in an irradiation direction (optical axis I) for the plurality of fingers 111 to 113. With this configuration, the light sources which irradiate light including a particular wavelength can be applied to the photographing apparatus 100.

(9) Further, in the photographing apparatus 100 according to Item (8), the second optical filter 104 is a filter configured to pass visible light. With this configuration, the patterns (fingerprints) of the back surfaces of the fingers 111 to 113 can be photographed.

(10) Further, in the photographing apparatus 100 according to Item (8), the second optical filter 104 is a filter configured to pass near-infrared light. With this configuration, the blood vessels of the fingers 111 to 113 can be photographed.

(11) Further, in the photographing apparatus 100 according to Item (2), a first wavelength of a first irradiation light from first light sources (102-1, 102-2) and a second wavelength of a second irradiation light from second light sources (102-4, 102-5) are different, the first light sources being arranged in the longitudinal direction X of the plurality of fingers 111 to 113, the second light sources being arranged in the longitudinal direction of the plurality of fingers 111 to 113 and closer to a base side of the plurality of fingers 111 to 113 than the first light sources are. With this configuration, light having different wavelengths of light can be irradiated on the fingers 111 to 113 depending on the irradiation position on the fingers 111 to 113.

(12) Further, in the photographing apparatus 100 according to Item (11), the first irradiation light is visible light, and the second irradiation light is near-infrared light. With this configuration, the patterns (fingerprints) and vessels of the back surfaces of the fingers 111 to 113 can be photographed.

(13) Further, the photographing apparatus 100 according to Item (1) may further include a fingertip presentation plate 1400 on which the plurality of fingers 111 to 113 are placeable, and through which light from the plurality of light sources 102 is transmitted. With this configuration, the user can be guided to present the fingertips on the fingertip presentation plate 1400. Further, the light source 1600 which irradiates the inside of the fingertip presentation plate 1400 may be provided. With this configuration, the insufficient amount of light on the fingertip side can be inhibited, and the amounts of light can be uniformalized over the fingers 111 to 113.

(14) Further, the photographing apparatus 100 according to Item (1) may further include a light source control module 300 configured to control amounts of irradiation light from the plurality of light sources 102 to be increased or reduced. With this configuration, the photographing apparatus 100 can autonomously increase or reduce the amounts of irradiation light. Further, the photographing apparatus 100 may include the distance sensor 600 which measures the distance D to the plurality of fingers 111 to 113. With this configuration, the light source control module 300 can control the amount of irradiation light to be increased or reduced for each of the light sources 102 depending on the distance D. For example, the light source control module 300 controls the increase or reduction so that an amount of irradiation light of a light source 102 at a longer distance D to the fingers 111 to 113 is larger than an amount of irradiation light of a light source 102 at a shorter distance D to the fingers 111 to 113. With this configuration, even in the case in which the plurality of fingers 111 to 113 are not at equal distance from the imaging unit 101, an even amount of light can be irradiated on the plurality of fingers 111 to 113 to be photographed by adjusting the amounts of light.

(15) Further, for example, the above-mentioned authentication apparatus 108 includes: an imaging unit 101 which is arranged at a position opposed to a plurality of fingers 111 to 113 to be presented, and is configured to image the plurality of fingers 111 to 113; a plurality of light sources 102 which are arranged in plurality in an array direction of the plurality of fingers 111 to 113, and are configured to irradiate the plurality of fingers 111 to 113 with light from an outside of an opposing region 130 in which the imaging unit 101 is opposed to the plurality of fingers 111 to 113 toward an inside of the opposing region 130; an image processing module (controller 107, computer 310) configured to generate image data of the plurality of fingers 111 to 113 based on an output signal from the imaging unit 101; and an authentication module configured to authenticate the plurality of fingers 111 to 113 based on first image data of the plurality of fingers 111 to 113 generated by the image processing module (controller 107, computer 310), and second image data of the plurality of fingers 111 to 113 generated by the image processing module (controller 107, computer 310). With this configuration, the light sources 102 can irradiate light not only on the back surfaces of the fingers 111 to 113 but also on side surfaces of the fingers 111 to 113. Consequently, the finger image obtained from the finger image data can be increased in clarity, and authentication accuracy can be increased.

It should be noted that this disclosure is not limited to the above-mentioned embodiments, and encompasses various modification examples and the equivalent configurations within the scope of the appended claims without departing from the gist of this disclosure. For example, the above-mentioned embodiments are described in detail for a better understanding of this disclosure, and this disclosure is not necessarily limited to what includes all the configurations that have been described. Further, a part of the configurations according to a given embodiment may be replaced by the configurations according to another embodiment. Further, the configurations according to another embodiment may be added to the configurations according to a given embodiment. Further, a part of the configurations according to each embodiment may be added to, deleted from, or replaced by another configuration.

Further, a part or entirety of the respective configurations, functions, processing modules, processing means, and the like that have been described may be implemented by hardware, for example, may be designed as an integrated circuit, or may be implemented by software by a processor interpreting and executing programs for implementing the respective functions.

The information on the programs, tables, files, and the like for implementing the respective functions can be stored in a storage device such as a memory, a hard disk drive, or a solid state drive (SSD) or a recording medium such as an IC card, an SD card, or a DVD.

Further, control lines and information lines that are assumed to be necessary for the sake of description are described, but not all the control lines and information lines that are necessary in terms of implementation are described. It may be considered that almost all the components are connected to one another in actuality.

What is claimed is:

1. A photographing apparatus, comprising:
a housing;
an image sensor configured to obtain a blood vessel image of a plurality of fingers;
a first light source;
a second light source; and
an upper plate portion of the housing;
wherein the image sensor, the first light source and the second light source are arranged in the housing;
wherein a first optical axis of the first light source is tilted in a first direction where the second light source is present so that the first optical axis intersects the upper plate portion, a second optical axis of the second light source is tilted in a second direction where the first light source is present so that the second optical axis intersects the upper plate portion; and
wherein the image sensor is configured to receive reflected light from the plurality of fingers which is irradiated with light from the first light source and the second light source.

2. A photographing apparatus, comprising:
a housing;
an image sensor configured to obtain a fingerprint image of a plurality of fingers;
a first light source;
a second light source; and
an upper plate portion of the housing;
wherein the image sensor, the first light source and the second light source are arranged in the housing;
wherein a first optical axis of the first light source is tilted in a first direction where the second light source is present so that the first optical axis intersects the upper plate portion, a second optical axis of the second light source is tilted in a second direction where the first light source is present so that the second optical axis intersects the upper plate portion; and wherein the image sensor is configured to receive reflected light from the plurality of fingers which is irradiated with light from the first light source and the second light source.

3. The photographing apparatus according to claim 1, wherein the image sensor is further configured to obtain a fingerprint image of the plurality of fingers.

4. The photographing apparatus according to claim 1, further comprising:
- a third light source arranged in a direction perpendicular to the first direction and in a direction horizontal to a mounting surface of the housing; and
- a fourth light source arranged in a direction perpendicular to the second direction and in the direction horizontal to the mounting surface of the housing;
- wherein a third optical axis of the third light source is tilted in a third direction where the fourth light source is present so that the third optical axis intersects the upper plate portion, and a fourth optical axis of the fourth light source is tilted in a fourth direction where the third light source is present so that the fourth optical axis intersects the upper plate portion.

5. The photographing apparatus according to claim 2, further comprising:
- a third light source arranged in a direction perpendicular to the first direction and in a direction horizontal to a mounting surface of the housing; and
- a fourth light source arranged in a direction perpendicular to the second direction and in the direction horizontal to the mounting surface of the housing;
- wherein a third optical axis of the third light source is tilted in a third direction where the fourth light source is present so that the third optical axis intersects the upper plate portion, and a fourth optical axis of the fourth light source is tilted in a fourth direction where the third light source is present so that the fourth optical axis intersects the upper plate portion.

6. The photographing apparatus according to claim 3, further comprising:
- a third light source arranged in a direction perpendicular to the first direction and in a direction horizontal to a mounting surface of the housing; and
- a fourth light source arranged in a direction perpendicular to the second direction and in the direction horizontal to the mounting surface of the housing;
- wherein a third optical axis of the third light source is tilted in a third direction where the fourth light source is present so that the third optical axis intersects the upper plate portion, and a fourth optical axis of the fourth light source is tilted in a fourth direction where the third light source is present so that the fourth optical axis intersects the upper plate portion.

7. The photographing apparatus according to claim 4, wherein a first amount of a first irradiation light from the first light source and the second light source is different from a second amount of a second irradiation light from the third light source and the fourth light source.

8. The photographing apparatus according to claim 7, wherein the first amount of irradiation light is larger than the second amount of irradiation light.

9. The photographing apparatus according to claim 1, wherein the first light source and the second light source are configured to irradiate visible light.

10. The photographing apparatus according to claim 2, wherein the first light source and the second light source are configured to irradiate visible light.

11. The photographing apparatus according to claim 3, wherein the first light source and the second light source are configured to irradiate visible light.

12. The photographing apparatus according to claim 1, wherein the first light source and the second light source are configured to irradiate near-infrared light.

13. The photographing apparatus according to claim 2, wherein the first light source and the second light source are configured to irradiate near-infrared light.

14. The photographing apparatus according to claim 3, wherein the first light source and the second light source are configured to irradiate near-infrared light.

15. The photographing apparatus according to claim 1, wherein the first light source and the second light source include a filter configured to pass light having a particular wavelength in a direction away from a mounting surface of the housing.

16. The photographing apparatus according to claim 2, wherein the first light source and the second light source include a filter configured to pass light having a particular wavelength in a direction away from a mounting surface of the housing.

17. The photographing apparatus according to claim 3, wherein the first light source and the second light source include a filter configured to pass light having a particular wavelength in a direction away from a mounting surface of the housing.

18. The photographing apparatus according to claim 15, wherein the filter is configured to pass visible light.

19. The photographing apparatus according to claim 15, wherein the filter is configured to pass near-infrared light.

20. The photographing apparatus according to claim 7, wherein a first wavelength of the first irradiation light is different from a second wavelength of the second irradiation light.

21. The photographing apparatus according to claim 19, wherein the first irradiation light is visible light, and the second irradiation light is near-infrared light.

22. The photographing apparatus according to claim 1, further comprising:
- a fingertip presentation portion provided to the housing, the fingertip presentation portion providing a surface for placement of fingertips of the plurality of the fingers;
- wherein the fingertip presentation portion is arranged at an opposite end of the housing from a mounting surface of the housing with respect to the first light source and the second light source; and
- wherein the first optical axis of the first light source is tilted in the first direction so that the first optical axis intersects the fingertip presentation portion, the second optical axis of the second light source is tilted in the second direction so that the second optical axis intersects the fingertip presentation portion.

23. The photographing apparatus according to claim 2, further comprising:
- a fingertip presentation portion provided to the housing, the fingertip presentation portion providing a surface for placement of fingertips of the plurality of the fingers;
- wherein the fingertip presentation portion is arranged at an opposite end of the housing from a mounting surface of the housing with respect to the first light source and the second light source; and
- wherein the first optical axis of the first light source is tilted in the first direction so that the first optical axis intersects the fingertip presentation portion, the second optical axis of the second light source is tilted in the second direction so that the second optical axis intersects the fingertip presentation portion.

24. The photographing apparatus according to claim 1, further comprising:
a controller programmed to control amounts of the light irradiated from the first light source and the second light source.

25. The photographing apparatus according to claim 2, further comprising:
a controller programmed to control amounts of the light irradiated from the first light source and the second light source.

26. The photographing apparatus according to claim 3, further comprising:
a controller programmed to control amounts of the light irradiated from the first light source and the second light source.

27. An authentication apparatus, comprising:
a housing;
an image sensor configured to obtain a blood vessel image of a plurality of fingers;
a first light source;
a second light source;
an upper plate portion of the housing;
a processor programmed to generate image data of the plurality of fingers based on an output signal from the image sensor; and
a controller programmed to authenticate the plurality of fingers based on first image data of the plurality of fingers generated by the processor, and second image data of the plurality of fingers generated by the processor;
wherein the image sensor, the first light source and the second light source are arranged in the housing;
wherein a first optical axis of the first light source is tilted in a first direction where the second light source is present so that the first optical axis intersects the upper plate portion, and a second optical axis of the second light source is tilted in a second direction where the first light source is present so that the second optical axis intersects the upper plate portion; and
wherein the image sensor is configured to receive reflected light from the plurality of fingers which is irradiated with light from the first light source and the second light source.

28. A photographing apparatus, comprising:
a housing;
an image sensor configured to obtain a fingerprint image of a plurality of fingers;
a first light source;
a second light source;
an upper plate portion of the housing;
a processor programmed to generate image data of the plurality of fingers based on an output signal from the image sensor; and
a controller programmed to authenticate the plurality of fingers based on first image data of the plurality of fingers generated by the processor, and second image data of the plurality of fingers generated by the processor;
wherein the image sensor, the first light source and the second light source are arranged in the housing;
wherein a first optical axis of the first light source is tilted in a first direction where the second light source is present so that the first optical axis intersects the upper plate portion, and a second optical axis of the second light source is tilted in a second direction where the first light source is present so that the second optical axis intersects the upper plate portion; and
wherein the image sensor is configured to receive reflected light from the plurality of fingers which is irradiated with light from the first light source and the second light source.

\* \* \* \* \*